US006737063B2

(12) United States Patent
Langermann et al.

(10) Patent No.: US 6,737,063 B2
(45) Date of Patent: May 18, 2004

(54) FIMH ADHESIN PROTEINS AND METHODS OF USE

(75) Inventors: Solomon Langermann, Baltimore, MD (US); Andrew Revel, Dallas, TX (US); Christine Auguste, Germantown, MD (US); Jeanne Burlein, Springfield, VA (US)

(73) Assignee: MedImmune, Inc., Gaithersburg, MD (US)

( * ) Notice: Subject to any disclaimer, the term of this patent is extended or adjusted under 35 U.S.C. 154(b) by 0 days.

(21) Appl. No.: 09/900,575

(22) Filed: Jul. 6, 2001

(65) Prior Publication Data

US 2002/0150587 A1 Oct. 17, 2002

Related U.S. Application Data

(60) Provisional application No. 60/216,750, filed on Jul. 7, 2000.

(51) Int. Cl.[7] ...................... A61K 39/02; A61K 39/395; A61K 31/70; C07H 21/04

(52) U.S. Cl. ................................ 424/190.1; 424/157.1; 424/169.1; 424/242.1; 424/257.1; 514/23; 514/25; 536/17.2; 536/17.9; 536/34.1; 536/23.1; 536/23.7; 536/24.1

(58) Field of Search ........................... 424/190.1, 157.1, 424/169.1, 242.1, 257.1; 514/23, 25; 536/17.2, 17.9, 34.1, 23.1, 23.7, 24.1

(56) References Cited

U.S. PATENT DOCUMENTS 6,500,434 B1 12/2002 Langermann

FOREIGN PATENT DOCUMENTS

| WO | WO 95/20657 | 8/1995 |
|---|---|---|
| WO | WO 01/04148 | 1/2001 |

OTHER PUBLICATIONS

Accession No.: AC P08191 or Krogfelt et al (Infect Immun Jun. 1990; 58(6): 1995–8).*

Langermann et al., "Vaccination with FimH Adhesin Protects Cynomolgus Monkeys From Colonization and Infection by Uropathogenic *Escherichia coli*" J. Infectious Diseases, vol. 181, pp. 774–778 (2000).

Palaszynski et al., "Systemic Immunization with Conserved Pilus–Associated Adhesins Protects Against Mucosal Infections," Dev. Biol. Stand. Basel, Karger, vol. 92, pp. 117–122 (1998).

Thankavel, et al., "Localization of a Domain in the FimH Adhesin of *Escherichia coli* Type 1 Fimbriae Capable of Receptor Recognition and use of a Domain–specific Antibody to Confer Protection against Experimental Urinary Tract Infection," American Society for Clinical Investigation, vol. 100, No. 5, pp. 1123–1136 (Sep. 1997).

Langermann et al., "Prevention of Mucosal *Escherichia coli* Infection by FimH–Adhesin–Based Systemic Vaccination," Science, vol. 276, pp. 607–611 (Apr. 25, 1997).

Jones, et al., "FimC is a periplasmic PapD–like chaperone that directs assembly of type 1 pili in bacteria," Proc. Nat'l/ Acad. Sci. USA, vol. 90, pp. 8397–8401 (Sep. 1993).

O'Hanley, et al, "Molecular Basis of *Escherichia coli* Colonization of the Upper Urinary Tract in BALB/c Mice," Amer. Society for Clinical Investigation, Inc., vol. 75, pp. 347–360 (Feb. 1985).

Tewari, et al., "Neutrophil Activation by Nascent FimH Subunits of Type 1 Fimbriae Purified from the Periplasm of *Escherichia coli*," Journal of Biological Chemistry, vol. 268, No. 4, pp. 3009–3015 (1993).

Knight, et al., "Crystallization and preliminary X–ray diffraction studies of the FimC–FimH chaperone–adhesin complex from *Escherichia coli*," Acta Crystallographica, Section D, pp. 207–210 (1997).

"Abstracts of the 89th Annual Meeting of the American Society for Microbiology," New Orleans, La, May 14–18, 1989.

Bereneice McClentton Madison, "Structural, Antigenic and Functional Analysis of FIMH Protein in *Escherichia coli* and Klebsiella Pneumoniae Type 1 Fimbriae," Univ. of Tennessee Cntr. for the Health Sciences, vol. 52/06–B, pages 2893, 159 pp. (1990).

Abraham, et al., "Conservation of the D–Mannose–adhesion protein among type 1 fimbriated members of the family Enterobacteriaceae," Nature, vol. 336 (Dec. 1988).

Abraham, et al., Protection Against *Escherichia coli*–Induced Urinary Tract Infections with Hybridoma Antibodies Directed Against Type 1 Fimbriae or Complementary D–Mannose Receptors, Infection and Immunity, vol. 48, No.3, pp. 625–628 (Jun. 1985).

* cited by examiner

*Primary Examiner*—Albert M Navarro
*Assistant Examiner*—Padma Baskar
(74) *Attorney, Agent, or Firm*—Elliot M. Olstein; Alan J. Grant

(57) ABSTRACT

The present invention provides bacterial immunogenic agents for administration to humans and non-human animals to stimulate an immune response. Also provided are methods for vaccination of mammalian species, especially human patients, with variants of the *E. coli* FimH protein, said variants being derived from different strains of *E. coli,* and to production of antibodies that protect the vaccine recipient against infection by pathogenic bacterial species. In another aspect the invention provides antibodies against such proteins and protein complexes that may be used as diagnostics and/or as protective/treatment agents for pathogenic bacterial species. A plasmid-based method of producing polypeptides, especially fused polypeptides, such as the complex of a bacterial chaperone and a bacterial adhesin, is also disclosed.

4 Claims, 17 Drawing Sheets

Figure 1(a)

| | | 1 … 90 |
|---|---|---|
| J96 | (1) | TTCGCCTGTAAAACCGCCAATGGTACCGCTATCCCTATTGGCGGTGGCAGCGCCAATGTTTATGTAAACCTTGCGCCCGTCGTGAATGTG |
| EC45 | (1) | TTCGCCTGTAAAACCGCCAATGGTACCGCAATCCCTATTGGCGGTGGCAGCGCCAATGTTTATGTAAACCTTGCGCCTGCCGTGAATGTG |
| B217 | (1) | TTCGCCTGTAAAACCGCCAATGGTACAGCTATCCCTATTGGCGGTGGCAGCGCTAATGTTTATGTAAACCTTGCGCCTGCCGTGAATGTG |
| DS17 | (1) | TTCGCCTGTAAAACCGCCAATGGTACCGCAATCCCTATTGGCGGTGGCAGCGCCAATGTTTATGTAAACCTTGCGCCTGCCGTGAATGTG |
| B212 | (1) | TTCGCCTGTAAAACCGCCAATGGTACCGCTATCCCTATTGGCGGTGGCAGCGCCAATGTTTATGTAAACCTTGCGCCTGCCGTGAATGTG |
| EC42 | (1) | TTCGCCTGTAAAACCGCCAATGGCACCGCTATCCCTATTGGCGGTGGCAGCGCCAATGTTTATGTAAACCTTGCGCCCGCCGTGAATGTG |
| EC56 | (1) | TTCGCCTGTAAAACCGCCAATGGTACCGCTATCCCTATTGGCGGTGGCAGCGCCAATGTTTATGTAAACCTTGCGCCCGTCGTGAATGTG |
| B210 | (1) | TTCGCCTGTAAAACCGCCAATGGTACCGCTATCCCTATTGGCGGTGGCAGCGCCAATGTTTATGTAAACCTTGCGCCCGTCGTGAATGTG |
| B203 | (1) | TTCGCCTGTAAAACCGCCAATGGTACCGCAATCCCTATTGGCGGTGGCAGCGCCAATGTTTATGTAAACCTTGCGCCTGCCGTGAATGTG |
| EC58 | (1) | TTCGCCTGTAAAACCGCCAATGGTACCGCAATCCCTATTGGCGGTGGCAGCGCCAATGTTTATGTAAACCTTGCGCCTGCCGTGAATGTG |
| EC60 | (1) | TTCGCCTGTAAAACCGCCAATGGCACCGCTATCCCTATTGGCGGTGGCAGCGCCAATGTTTATGTAAACCTTGCGCCCGCCGTGAATGTG |
| EC61 | (1) | TTCGCCTATAAAACCGCCAATGGTACCGCTATCCCTATTGGCGGTGGCAGCGCCAATGTTTATGTAAACCTTGCGCCCGCCGTGAATGTG |
| EC80 | (1) | TTCGCCTGTAAAACCGCCAATGGTACCGCTATCCCTATTGGCGGTGGCAGCGCCAATGTTTATGTAAACCTTGCGCCCGTCGTGAATGTG |
| EC95 | (1) | TTCGCCTGTAAAACCGCCAATGGTACCGCAATCCCTATTGGCGGTGGCAGCGCCAATGTTTATGTAAACCTTGCGCCTGCCGTGAATGTG |
| EC62 | (1) | ATCGCCTGTAAAACCGCCAATGGCACCGCTATCCCTATTGGCGGTGGCAGCGCCAATGTTTATGTAAACCTTGCGCCCGCCGTGAATGTG |
| B238 | (1) | TTCGCCTGTAAAACCGCCAATGGCACCGCTATCCCTATTGGCGGTGGCAGCGCCAATGTTTATGTAAACATTGCGCCCGCCGTGAATGTG |
| B240 | (1) | TTCGCCTGTAAAACCGCCAATGGTACCGCTATCCCTATTGGCGGTGGCAGCGCCAATGTTTATGTAAACCTTGCGCCCGTCGTGAATGTG |
| B242 | (1) | TTTGCCTGTAAAACCGCCAATGGCACCGCTATCCCTATTGGCGGTGGCAGCGCCAATGTTTATGTAAACTTGGCGCCCGCCGTGAATGTG |
| EC189 | (1) | TTCGCCTGTAAAACCGCCAATGGTACCGCTATCCCTATTGGCGGTGGCAGCGCTAATGTTTATGTAAACCTTGCGCCTGCCGTGAATGTG |

Figure 1(b)

```
                 91                                                                                       180
  J96     (91)  GGGCAAAACCTGGTCGTGGATCTTTCGACGCAAATCTTTTGCCATAACGATTATCCGGAAACCATTACAGACTATGTCACACTGCAACGA
 EC45     (91)  GGGCAAAACCTGGTCGTAGATCTTTCGACGCAAATCTTTTGCCATAACGATTACCCAGAAACCATTACAGACTATGTCACACTGCAACGA
 B217     (91)  GGGCAAAACCTGGTCGTAGATCTTTCGACGCAAATCTTTTGCCATAACGATTATCCGGAAACCATTACAGACTATGTCACACTGCAACGA
 DS17     (91)  GGGCAAAACCTGGTCGTAGATCTTTCGACGCAAATCTTTTGCCATAACGATTACCCAGAAACCATTACAGACTATGTCACACTGCAACGA
 B212     (91)  GGGCAAAACCTGGTCGTGGATCTTTCGACGCAAATCTTTTGCCATAACGATTACCCGGAAACCATTACAGACTATGTCACACTGCAACGA
 EC42     (91)  GGGCAAAACCTGGTCGTGGATCTTTCGACGCAAATCTTTTGCCATAACGATTACCCGGAAACCATTACAGATTATGTCACACTGCAACGA
 EC56     (91)  GGGCAAAACCTGGTCGTGGATCTTTCGACGCAAATCTTTTGCCATAACGATTATCCGGAAACCATTACAGACTATGTCACACTGCAACGA
 B210     (91)  GGGCAAAACCTGGTCGTGGATCTTTCGACGCAAATCTTTTGCCATAACGATTATCCGGAAACCATTACAGACTATGTCACACTGCAACGA
 B203     (91)  GGGCAAAACCTGGTCGTAGATCTTTCGACGCAAATCTTTTGCCATAACGATTACCCAGAAACCATTACAGACTATGTCACACTGCAACGA
 EC58     (91)  GGGCAAAACCTGGTCGTAGATCTTTCGACGCAAATCTTTTGCCATAACGATTACCCAGAAACCATTACAGACTATGTCACACTGCAACGA
 EC60     (91)  GGGCAAAACCTGGTCGTGGATCTTTCGACGCAAATCTTTTGCCATAACGATTACCCGGAAACCATTACAGATTATGTCACACTGCAACGA
 EC61     (91)  GGGCAAAACCTGGTCGTGGATCTTTCGACGCAAATCTTTTGCCATAACGATTATCCGGAAACCATTACAGACTATGTCACACTGCAACGA
 EC80     (91)  GGGCAAAACCTGGTCGTGGATCTTTCGACGCAAATCTTTTGCCATAACGATTATCCGGAAACCATTACAGACTATGTCACACTGCAACGA
 EC95     (91)  GGGCAAAACCTGGTCGTAGATCTTTCGACGCAAATCTTTTGCCATAACGATTACCCAGAAACCATTACAGACTATGTCACACTGCAACGA
 EC62     (91)  GGGCAAAACCTGGTCGTAGATCTTTCGACGCAAATCTTTTGCCATAACGATTACCCGGAAACCATTACAGACTATGTCACACTGCAACGA
 B238     (91)  GGGCAAAACCTGGTCGTGGATCTTTCGACGCAAATCTTTTGCCATAACGATTACCCGGAAACCATTACAGATTATGTCACACTGCAACGA
 B240     (91)  GGGCAAAACCTGGTCGTGGATCTTTCGACGCAAATCTTTTGCCATAACGATTATCCGGAAACCATTACAGACTATGTCACACTGCAACGA
 B242     (91)  GGGCAAAACCTGGTCGTGGATCTTTCGACGCAAACCTTTTGCCATAACGATTATCCGGAAACCATTACAGACTATGTCACACTGCAACGA
EC189     (91)  GGGCAAAACCTGGTCGTAGATCTTTCGACGCAAATCTTTTGCCATAACGATTATCCGGAAACCATTACAGACTATGTCACACTGCAACGA
```

Figure 1(c)

```
                181                                                                                       270
J96      (181) GGCTCGGCTTATGGCGGCGTGTTATCTAATTTTTCCGGGACCGTAAAATATAGTGGCAGTAGCTATCCATTTCCTACCACCAGCGAAACG
EC45     (181) GGTGCGGCTTATGGCGGCGTGTTATCTAGTTTTTCCGGGACCGTAAAATATAATGGCAGTAGCTATCCTTTCCCTACTACCAGCGAAACG
B217     (181) GGCTCGGCTTATGGCGGCGTGTTATCTAATTTTTCCGGGACCGTAAAATATAGTGGCAGTAGCTATCCATTTCCGACCACCAGCGAAACG
DS17     (181) GGTTCGGCTTATGGCGGCGTGTTATCTAGTTTTTCCGGGACCGTAAAATATAATGGCAGTAGCTATCCTTTCCCTACTACCAGCGAAACG
B212     (181) GGTTCGGCTTATGGCGGCGTGTTATCTAGTTTTTCCGGGATCGTAAAATATAATGGCAGTAGCTATCCTTTCCCTACTACCAGCGAAACG
EC42     (181) GGCTCGGCTTATGGCGGCGTGTTATCTAATTTTTCCGGGACCGTAAAATATAGTGGCAGTAGCTATCCATTTCCGACCACCAGTGAAACG
EC56     (181) GGCTCGGCTTATGGCGGCGTGTTATCTAATTTTTCCGGGACCGTAAAATATAGTGGCAGTAGCTATCCATTTCCTACCACCAGCGAAACG
B210     (181) GGCTCGGCTTATGGCGGCGTGTTATCTAATTTTTCCGGGATCGTAAAATATAGTGGCAGTAGCTATCCTTTCCCTACCACCAGCGAAACG
B203     (181) GGTGCGGCTTATGGCGGCGTGTTATCTAGTTTTTCCGGGACCGTAAAATATAATGGCAGTAGCTATCCTTTCCCTACTACCAGCGAAACG
EC58     (181) GGTTCGGCTTATGGCAGCGTGTTATCTAGTTTTTCCGGGACCGTAAAATATAATGGCAGTAGCTATCCTTTCCCTACTACCAGCGAAACG
EC60     (181) GGCTCGGCTTATGGCGGCGTGTTATCTAATTTTTCCGGGACCGTAAAATATAGTGGCAGTAGCTATCCATTTCCGACCACCAGTGAAACG
EC61     (181) GGCTCGGCTTATGGCGGCGTGTTATCTAATTTTTCCGGGACCGTAGAATATAGTGGCAGTAGCTATCCATTTCCTACCACCAGCGAAACG
EC80     (181) GGCTCGGCTTATGGCGGCGTGTTATCTAATTTTTCCGGGACCGTAAAATATAGTGGCAGTAGCTATCCATTTCCTACCACCAGCGAAACG
EC95     (181) GGTTCGGCTTATGGCGGCGTGTTATCTAGTTTTTCCGGGACCGTAAAATATAATGGCAGTAGCTATCCTTTCCCTACTACCAGCGAAACG
EC62     (181) GGTTCGGCTTATGGCGGCGTGTTATCTCATTTTTCCGGGACCGTAAAATATAGTGGCAGTAGCTATCCATTTCCTACCACCAGCGAAACG
B238     (181) GGCTCGGCTTATGGCGGCGTGTTATCTAATTTTTCCGGGACCGTAAAATATAGTGGCAGTAGCTATCCATTTCCGACCACCAGTGAAACG
B240     (181) GGCTCGGCTTATGGCGGCGTGTTATCTAATTTTTCCGGGACCGTAAAATATAGTGGCAGTAGCTATCCATTTCCTACCACCAGCGAAACG
B242     (181) GGCTCGGCTTATGGCGGCGTGTTATCTAATTTTTCCGGGACCGTAAAATATAGTGGCAGTAGCTATCCATTTCCGACTACCAGCGAAACG
EC189    (181) GGCTCGGCTTATGGCGGCGTGTTATCTAATTTTTCCGGGACCGTAAAATATAGTGGCAGTAGCTATCCATTTCCGACCACCAGCGAAACG
```

Figure 1(d)

```
                271                                                                                        360
J96     (271)  CCGCGCGTTGTTTATAATTCGAGAACGGATAAGCCGTGGCCGGTGGCGCTTTATTTGACGCCTGTGAGCAGTGCGGGCGGGGTGGCGATT
EC45    (271)  CCGCGGGTTGTTTATAATTCGAGAACGGATAAGCCGTGGCCGGTGGCGCTTTATTTGACGCCGGTGAGCAGTGCGGGGGGAGTGGCGATT
B217    (271)  CCGCGGGTTGTTTATAATTCGAGAACGGATAAGCCGTGGCCGGTGGCGCTTTATTTGACGCCTGTGAGCAGTGCGGGCGGGGTGGCGATT
DS17    (271)  CCGCGGGTTGTTTATAATTCGAGAACGGATAAGCCGTGGCCGGTGGCGCTTTATTTGACGCCGGTGAGCAGTGCGGGGGGAGTGGCGATT
B212    (271)  CCGCGGGTTGTTTATAATTCGAGAACGGATAAGCCGTGGCCGGTGGCGCTTTATTTGACGCCTGTGAGCAGTGCGGGGGGAGTGGCGATT
EC42    (271)  CCGCGGGTTGTTTATAATTCGAGAACGGATAAGCCGTGGCCGGTGGCGCTTTATTTGACGCCTGTGAGCAGTGCGGGCGGGGTGGTGATT
EC56    (271)  CCGCGCGTTGTTTATAATTCGAGAACGGATAAGCCGTGGCCGGTGGCGCTTTATTTGACGCCTGTGAGCAGTGCGGGCGGGGTGGCGATT
B210    (271)  CCGCGCGTTGTTTATAATTCGAGAACGGATAAGCCGTGGCCGGTGGCGCTTTATTTGACGCCTGTGAGCAGTGCGGGGGGAGTGGCGATT
B203    (271)  CCGCGGGTTGTTTATAATTCGAGAACGGATAAGCCGTGGCCGGTGGCGCTTTATTTGACGCCGGTGAGCAGTGCGGGGGGAGTGGCGATT
EC58    (271)  CCGCGGGTTGTTTATAATTCGAGAACGGATAAGCCGTGGCCGGTGGCGCTTTATTTGACGCCGGTGAGCAGTGCGGGGGGAGTGGCGATT
EC60    (271)  CCGCGGGTTGTTTATAATTCGAGAACGGATAAGCCGTGGCCGGTGGCGCTTTATTTGACGCCTGTGAGCAGTGCGGGCGGGGTGGTGATT
EC61    (271)  CCGCGCGTTGTTTATAATTCGAGAACGGATAAGCCGTGGCCGGTGGCGCTTTATTTGACGCCTGTGAGCAGTGCGGGCGGGGTGGCGATT
EC80    (271)  CCGCGCGTTGTTTATAATTCGAGAACGGATAAGCCGTGGCCGGTGGCGCTTTATTTGACGCCTGTGAGCAGTGCGGGCGGGGTGGCGATT
EC95    (271)  CCGCGGGTTGTTTATAATTCGAGAACGGATAAGCCGTGGCCGGTGGCGCTTTATTTGACGCTGGTGAGCAGTGCGGGGGGAGTGGCGATT
EC62    (271)  CCGCGCGTTGTTTATAATTCGAGAACGGATAAGCCGTGGCCGGTGGCGCTTTATTTGACGCCTGTGAGCAGTGCGGGTGGGGTGGCGATT
B238    (271)  CCGCGGGTTGTTTATAATTCGAGAACGGATAAGCCGTGGCCGGTGGCGCTTTATTTGACGCCTGTGAGCAGTGCGGGCGGGGTGGTGATT
B240    (271)  CCGCGCGTTGTTTATAATTCGAGAACGGATAAGCCGTGGCCGGTGGCGCTTTATTTGACGCCTGTGAGCAGTGCGGGCGGGTTGGTGATT
B242    (271)  CCGCGGGTTGTTTATAATTCGAGAACGGATAAGCCGTGGCCGGTGGCGCTTTATTTGACGCCTGTGAGCAGTGCGGGTGGGGTGGCGATT
EC189   (271)  CCGCGGGTTGTTTATAATTCGAGAACGGATAAGCCGTGGCCGGTGGCGCTTTATTTGACGCCTGTGAGCAGTGCGGGCGGGGTGGCGATT
```

Figure 1(e)

```
                361                                                                                       450
  J96   (361) AAAGCTGGCTCATTAATTGCCGTGCTTATTTTGCGACAGACCAACAACTATAACAGCGATGATTTCCAGTTTGTGTGGAATATTTACGCC
 EC45   (361) AAAGCTGGCTCATTAATTGCCGTGCTTATTTTGCGACAGACCAACAACTATAACAGCGATGATTTCCAGTTTGTGTGGAATATTTACGCC
 B217   (361) AAAGCTGGCTCATTAATTGCCGTGCTTATTTTGCGACAGACCAACAACTATAACAGCGATGATTTCCAGTTTGTGTGGAATATTTACGCC
 DS17   (361) AAAGCTGGCTCATTAATTGCCGTGCTTATTTTGCGACAGACCAACAACTATAACAGCGATGATTTCCAGTTTGTGTGGAATATTTACGCC
 B212   (361) AAAGCAGGCTCATTAATTGCCGTGCTTATTTTGCGACAGACCAACAACTATAACAGCGATGATTTCCAGTTTGTGTGGAATATTTACGCC
 EC42   (361) AAAGCTGGCTCATTAATTGCCGTGCTTATTTTGCGACAGACCAACAACTATAACAGCGATGATTTCCAGTTTGTGTGGAATATTTACGCC
 EC56   (361) AAAGCTGGCTCATTAATTGCCGTGCTTATTTTGCGACAGACCAACAACTATAACAGCGATGATTTCCAGTTTGTGTGGAATATTTACGCC
 B210   (361) AAAGCAGGCTCATTAATTGCCGTGCTTATTTTGCGACAGACCAACAACTATAACAGCGATGGTTTCCAGTTTGTGTGGAATATTTACGCC
 B203   (361) AAAGCTGGCTCATTAATTGCCGTGCTTATTTTGCGACAGACCAACAACTATAACAGCGATGATTTCCAGTTTGTGTGGAATATTTACGCC
 EC58   (361) AAAGCTGGCTCATTAATTGCCGTGCTTATTTTGCGACAGACCAACAACTATAACAGCGATGATTTCCAGTTTGTGTGGAATATTTACGCC
 EC60   (361) AAAGCTGGCTCATTAATTGCCGTGCTTATTTTGCGACAGACCAACAACTATAACAGCGATGATTTCCAGTTTGTGTGGAATATTTACGCC
 EC61   (361) AAAGCTGGCTCATTAATTGCCGTGCTTATTTTGCGACAGACCAACAACTATAACAGCGATGATTTCCAGTTTGTGTGGAATATTTACGCC
 EC80   (361) AAAGCTGGCTCATTAATTGCCGTGCTTATTTTGCGACAGACCAACAACTATAACAGCGATGATTTCCAGTTTGTGTGGAATATTTACGCC
 EC95   (361) AAAGCTGGCTCATTAATTGCCGTGCTTATTTTGCGACAGACCAACAACTATAACAGCGATGATTTCCAGTTTGTGTGGAATATTTACGCC
 EC62   (361) AAGGCTGGCTCATTAATGGCTGTGCTAATTTTGCGACAGACCAATAACTATAACAGCGATGATTTCCAGTTTGTGTGGAATATTTACGCC
 B238   (361) AAAGCTGGCTCATTAATTGCCGTGCTTATTTTGCGACAGACCAACAACTATAACAGCGATGATTTCCAGTTTGTGTGGAATATTTACGCC
 B240   (361) AAAGCTGGCTCATTAATTGCCGTGCTTATTTTGCGACAGACCAACAACTATAACAGCGATGATTTCCAGTTTGTGTGGAATATTTACGCC
 B242   (361) AAAGCTGGCTCATTAATTGCCGTGCTTATTTTGCGACAGACCAACAACTATAACAGCGATGATTTCCAGTTTGTGTGGAATATTTACGCC
EC189   (361) AAAGCTGGCTCATTAATTGCCGTGCTTATTTTGCGACAGACCAAAAACTATAACAGCGATGATTTCCAGTTTGTGTGGAATATTTACGCC
```

Figure 1(f)

```
                451                                                                                      540
  J96   (451) AATAATGATGTGGTGGTGCCTACTGGCGGCTGCGATGTTTCTGCTCGTGATGTCACCGTTACTCTGCCGGACTACCCTGGTTCAGTGCCA
 EC45   (451) AATAATGATGTGGTGGTGCCCACTGGCGGCTGCGATGTTTCTGCTCGTGATGTCACCGTTACTCTGCCGGACTACCCTGGTTCAGTGCCG
 B217   (451) AATAATGATGTGGTGGTGCCTACTGGCGGCTGCGATGTTTCTGCTCGTGATGTCACCGTTACTCTGCCGGACTACCCTGGTTCAGTGCCA
 DS17   (451) AATAATGATGTGGTGGTGCCCACTGGCGGCTGTGATGCTTCTGCTCGTGATGTCACCGTTACTTTGCCGGACTACCCTGGTTCAGTGCCG
 B212   (451) AATAATGATGTGGTGGTGCCCACTGGCGGCTGCGATGCTTCTGCTCGTGATGTCACCGTTACTCTGCCGGACTACCCTGGTTCAGTGCCG
 EC42   (451) AATAATGATGTGGTGGTGCCCACTGGCGGCTGCGATGTTTCTGCTCGTGATGTCACCGTTACTCTGCCGGACTACCCTGGTTCAGTGCCG
 EC56   (451) AATAATGATGTGGTGGTGCCTACTGGCGGCTGCGATGTTTCTGCTCGTGATGTCACCGTTACTCTGCCGGACTACCCTGGTTCAGTGCCA
 B210   (451) AATAATGATGTGGTGGTGCCCACTGGCGGCTGCGATGCTTCTGCTCGTGATGTCACCGTTACTCTGCCGGACTACCCTGGTTCAGTGCCG
 B203   (451) AATAATGATGTGGTGGTGCCCACTGGCGGCTGCGATGTTTCTGCTCGTGATGTCACCGTTACTCTGCCGGACTACCCTGGTTCAGTGCCG
 EC58   (451) AATAATGATGTGGTGGTGCCCACTGGCGGCTGTGATGTTTCTGCTCGTGATGTCACCGTTACTCTGCCGGACTACCCTGGTTCAGTGCCG
 EC60   (451) AATAATGATGTGGTGGTGCCCACTGGCGGCTGCGATGTTTCTGCTCGTGATGTCACCGTTACTCTGCCGGACTACCCTGGTTCAGTGCCG
 EC61   (451) AATAATGATGTGGTGGTGCCTACTGGCGGCTGCGATGTTTCTGCTCGTGATGTCACCGTTACTCTGCCGGACTACCCTGGTTCAGTGCCA
 EC80   (451) AATAATGATGTGGTGGTGCCTACTGGCGGCTGCGATGTTTCTGCTCGTGATGTCACCGTTACTCTGCCGGACTACCGTGGTTCAGTGCCA
 EC95   (451) AATAATGATGTGGTGGTGCCCACTGGCGGCTGTGATGTTTCTGCTCGTGATGTCACCGTTACTCTGCCGGACTACCCTGGTTCAGTGCCG
 EC62   (451) AATAATGATGTGGTGGTGCCCACTGGCGGCTGTGATGTTTCTGCTCGTGATGTCACCGTTACTCTGCCAGACTACCCTGGTTCAGTGCCG
 B238   (451) AATAATGATGTGGTGGTGCCCACTGGCGGCTGCGATGTTTCTGCTCGTGATGTCACCGTTACTCTGCCGGACTACCCTGGTTCAGTGCCG
 B240   (451) AATAATGATGTGGTGGTGCCTACTGGCGGCTGCGATGTTTCTGCTCGTGATGTCACCGTTACTCTGCCGGACTACCGTGGTTCAGTGCCA
 B242   (451) AATAATGATGTGGTGGTGCCTACTGGCGGCTGCGATGTTTCTGCTCATGATGTCACCGTTACTCTGCCGGACTACCCTGGTTCAGTGCCA
EC189   (451) AATAATGATGTGGTAGTGCCTACTGGCGGCTGCGATGTTTCTGCTCGTGATGTCACCGTTACTCTGCCGGACTACCCTGGTTCAGTGCCA
```

Figure 1(g)

```
                541                                                                                        630
  J96    (541)  ATTCCTCTTACCGTTTATTGTGCGAAAAGCCAAAACCTGGGGTATTACCTCTCCGGCACAACCGCAGATGCGGGCAACTCGATTTTCACC
 EC45    (541)  ATTCCTCTTACCGTTTATTGTGCGAAAAGCCAAAACCTGGGGTATTACCTCTCCGGCACAACCGCAGATGCGGGCAACTCGATTTTCACC
 B217    (541)  ATTCCTCTTACCGTTTATTGTGCGAAAAGCCAAAACCTGGGGTATTACCTCTCCGGCACAACCGCAGATGCGGGCAACTCGATTTTCACC
 DS17    (541)  ATTCCTCTTACCGTTTATTGTGCGAAAAGCCAAAACCTGGGGTATTACCTATCCGGCACAACCGCAGATGCGGGCAACTCGATTTTCACC
 B212    (541)  ATTCCTCTTACCGTTTATTGTGCGAAAAGCCAAAACCTGGGGTATTACCTCTCCGGCACAACCGCAGATGCGGGCAACTCGATTTTCACC
 EC42    (541)  ATTCCTCTTACCGTTTATTGTGCGAAAAGCCAAAACCTGGGGTATTACCTCTCCGGCACAACCGCAGATGCGGGCAACTCGATTTTCACC
 EC56    (541)  ATTCCTCTTACCGTTTATTGTGCGAAAAGCCAAAACCTGGGGTATTACCTCTCCGGCACAACCGCAGATGCGGGCAACTCGATTTTCACC
 B210    (541)  ATTCCTCTTACCGTTTATTGTGCGAAAAGCCAAAACCTGGGGTATTACCTCTCCGGCACAACCGCAGGTGCGGGCAACTCGATTTTCACC
 B203    (541)  ATTCCTCTTACCGTTTATTGTGCGAAAAGCCAAAACCTGGGGTATTACCTCTCCGGCACAACCGCAGATGCGGGCAACTCGATTTTCACC
 EC58    (541)  ATTCCTCTTACCGTTTATTGTGCGAAAAGCCAAAACCTGGGGTATTACCTATCCGGCACAACCGCAGATGCGGGCAACTCGATTTTCACC
 EC60    (541)  ATTCCTCTTACCGTTTATTGTGCGAAAAGCCAAAACCTGGGGTATTACCTCTCCGGCACAACCGCAGATGCGGGCAACTCGATTTTCACC
 EC61    (541)  ATTCCTCTTACCGTTTATTGTGCGAAAAGCCAAAACCTGGGGTATTACCTCTCCGGCACAACCGCAGATGCGGGCAACTCGATTTTCACC
 EC80    (541)  ATTCCTCTTACCGTTTATTGTGCGAAAAGCCAAAACCTGGGGTATTACCTCTCCGGCACACACGCAGATGCGGGCAACTCGATTTTCACC
 EC95    (541)  ATTCCTCTTACCGTTTATTGTGCGAAAAGCCAAAACCTGGGGTATTACCTATCCGGCACAACCGCAGATGCGGGCAACTCGATTTTCACC
 EC62    (541)  ATTCCTCTTACCGTTTATTGTGCGAAAAGCCAAAACCTGGGGTATTACCTCTCCGGCACAACCGCAGATGCGGGCAACTCGATTTTCACC
 B238    (541)  ATTCCTCTTACCGTTTATTGTGCGAAAAGCCAAAACCTGGGGTATTACCTCTCCGGCACAACCGCAGATGCGGGCAACTCGATTTTCACC
 B240    (541)  ATTCCTCTTACCGTTTATTGTGCGAAAAGCCAAAACCTGGGGTATTACCTCTCCGGCACAACCGCAGATGCGGGCAACTCGATTTTCACC
 B242    (541)  ATTCCTCTTACCGTTTATTGTGCGAAAAGCCAAAACCTGGGGTATTACCTCTCCGGCACAACCGCAGATGCGGGCAACTCGATTTTCACC
EC189    (541)  ATTCCTCTTACCGTTTATTGTGCGAAAAGCCAAAACCTGGGGTATTACCTCTCCGGCACAACCGCAGATGCGGGCAACTCGATTTTCACC
```

Figure 1(h)

```
             631                                                                                      720
J96    (631) AATACCGCGTCGTTTTCACCTGCACAGGGCGTCGGCGTACAGTTGACGCGCAACGGTACGATTATTCCAGCGAATAACACGGTATCGTTA
EC45   (631) AATACCGCGTCGTTTTCACCCGCGCAGGGCGTCGGCGTACAGTTGACGCGCAACGGTACGATTATTCCAGCGAATAACACGGTATCGTTA
B217   (631) AATACCGCGTCGTTTTCACCAGCGCAGGGCGTCGGCGTTCAGTTGACGCGCAACGGTACGATTATTCCCACGAATAACACGGTATCGTTA
DS17   (631) AATACCGCGTCGTTTTCACCCGCGCAGGGCGTCGGCGTACAGTTGACGCGCAACGGTACGATTATTCCAGCGAATAACACGGTATCGTTA
B212   (631) AATACCGCGTCGTTTTCACCCGCGCAGGGCGTCGGCGTACAGTTGACGCGCAACGGTACGATTATTCCAGCGAATAACACGGTATCGTTA
EC42   (631) AATACCGCGTCGTTTTCACCTGCACAGGGCGTCGGCGTACAGTTGACGCGCAACGGTACGATTATTCCAGCGAATAACACGGTATCGTTA
EC56   (631) AATACCGCGTCGTTTTCACCTGCACAGGGCGTCGGCGTACAGTTGACGCGCAACGGTACGATTATTCCAGCGAATAACACGGTATCGTTA
B210   (631) AATACCGCGTCGTTTTCACCCGCGCAGGGCGTCGGCGTACAGTTGGCGCGCAACGGTACGGTTATTCCAGCGAATAACACGGTATCGTTA
B203   (631) AATACCGCGTCGTTTTCACCCGCGCAGGGCGTCGGCGTACAGTTGACGCGCAACGGTACGATTATTCCAGCGAATAACACGGTATCGTTA
EC58   (631) AATACCGCGTCGTTTTCACCCGCGCAGGGCGTCGGCGTACAGTTGACGCGCAACGGTACGATTATTCCAGCGAATAACACGGTATCGTTA
EC60   (631) AATACCGCGTCGTTTTCACCTGCACAGGGCGTCGGCGTACAGTTGACGCGCAACGGTACGATTATTCCAGCGAATAACACGGTATCGTTA
EC61   (631) AATACCGCGTCGTTTTCACCTGCACAGGGCGTCGGCGTACAGTTGACGCGCAACGGTACGATTATTCCAGCGAATAACACGGTATCTTTA
EC80   (631) AATACCGCGTCGTTTTCACCTGCACAGGGCGTCGGCGTACAGTTGACGCGCAACGGTACGATTATTCCAGCGAATAACACGGTATCGTTA
EC95   (631) AATACCGCGTCGTTTTCACCCGCGCAGGGCGTCGGCGTACAGTTGACGCGCAACGGTACGATTATTCCAGCGAATAACACGGTATCGTTA
EC62   (631) AATACCGCGTCGTTTTCACCTGCACAGGGCGTCGGCGTACAGTTAACGCGCAACGGTACGATTAATCCAGCGAATAACACGGTATCGTTA
B238   (631) AATACCGCGTCGTTTTCACCTGCACAGGGCGTCGGCGTACAGTTGACGCGCAACGGTACGATTATTCCAGCGAATAACACGGTATCGTTA
B240   (631) AATACCGCGTCGTTTTCACCTGCACAGGGCGTCGGCGTACAGTTGACGCGCAACGGTACGATTATTCCAACGAATAACACGGTATCGTTA
B242   (631) AATACCGCGTCGTTTTCACCAGCGCAGGGCGTCGGCGTACAGTTGACGCGCAACGGTACGATTATTCCAGCGAATAACACGGTATCGTTA
EC189  (631) AATACCGCGTCGTTTTCACCAGCGCAGGGCGTCGGCGTACAGTTGACGCGCAACGGTACGATTATTCCAGCGAATAACACGGTATCGTTA
```

Figure 1(i)

```
                721                                                                                        810
J96     (721)   GGAGCAGTAGGGACTTCGGCGGTGAGTCTGGGATTAACGGCAAATTATGCACGTACCGGAGGGCAGGTGACTGCAGGGAATGTGCAATCG
EC45    (721)   GGAGCAGTAGGGACTTCGGCGGTAAGTCTGGGATTAACGGCAAATTACGCACGTACCGGAGGGCAGGTGACTGCAGGGAATGTGCAATCG
B217    (721)   GGAGCAGTACGGACTTCGGCGGTAAGTCTGGGATTAACGGCAAATTACGCACGTACCGGAGGGCAGGTGACTGCAGGGAATGTGCAATCG
DS17    (721)   GGAGCAGTAGGGACTTCGGCGGTAAGTCTGGGATTAACGGCAAATTACGCACGTACCGGAGGGCAGGTGACTGCAGGGAATGTGCAATCG
B212    (721)   GGAGCAGTAGGGACTTCGGCGGTAAGTCTGGGATTAACGGCAAATTACGCACGTACCGGAGGGCAGGTGACTGCAGGGAATGTGCAATCG
EC42    (721)   GGAGCAGTAGGGACTTCGGCGGTAAGTCTGGGATTAACGGCAAATTACGCACGTACCGGAGGGCAGGTGACTGCAGGGAATGTGCAATCG
EC56    (721)   GGAGCAGTAGGGACTTCGGCGGTGAGTCTGGGATTAACGGCAAATTATGCACGTACCGGAGGGCAGGTGACTGCAGGGAATGTGCAATCG
B210    (721)   GGAGCAGTAGGGACTTCGGCGGTGAGTCTGGGATTAACGGCAAATTACGCACGTACCGGAGGGCAGGTGACTGCAGGGAATGTGCAATCG
B203    (721)   GGAGCAGTAGGGACTTCGGCGGTAAGTCTGGGATTAACGGCAAATTACGCACGTACCGGAGGGCAGGTGACTGCAGGGAATGTGCAATCG
EC58    (721)   GGAGCAGTAGGGACTTCGGCGGTAAGTCTGGGATTAACGGCAAATTACGCACGTACCGGAGGGCAGGTGACTGCAGGGAATGTGCAATCG
EC60    (721)   GGAGCAGTAGGGACTTCGGCGGTAAGTCTGGGATTAACGGCAAATTACGCACGTACCGGAGGGCAGGTGACTGCAGGGAATGTGCGATCG
EC61    (721)   GGAGCAGTAGGGACTTCGGCGGTGAGTCTGGGATTAACGGCAAATTATGCACGTACCGGAGGGCAGGTGACTGCAGGGAATGTGCAATCG
EC80    (721)   GGAGCAGTAGGGACTTCGGCGGTGAGTCTGGGATTAACGGCAAATTATGCACGTACCGGAGGGCAGGTGACTGCAGGGAATGTGCAATCG
EC95    (721)   GGAGCAGTAGGGACTTCGGCGGTAAGTCTGGGATTAACGGCAAATTACGCACGTACCGGAGGGCAGGTGACTGCAGGGAATGTGCAATCG
EC62    (721)   GGAGCAGTAGGGACTTCGGCGGTAAGTCTGGGATTAACGGCAAATTACGCACGTACCGGAGGGCAGGTGACTGCAGGGAATGTGCAATCG
B238    (721)   GGAGCAGTAGGGACTTCGGCGGTAAGTCTGGGATTAACGGCAAATTACGCACGTACCGGAGGGCAGGTGACTGCAGGGAATGTGCAATCG
B240    (721)   GGAGCAGTAGGGACTTCGGCGGTAAGTCTGGGATTAACGGCAAATTACGCACGTACCGGAGGGCAGGTGACTGCAGGGAATGTGCAATCG
B242    (721)   GGAGCAGTAGGGACTTCGGCGGTGAGTCTGGGATTAACGGCAAATTACGCACGTACCGGAGGGCAGGTGACTGCAGGGAATGTGCAATCG
EC189   (721)   GGAACAGTAGGAACTTCGGCGGTAAGTCTGGGATTAACGGCAAATTACGCACGTACCGGCGGGCAGGTGACTGCAGGGAATGTGCAATCG
```

Figure 1(j)

```
                   811                       837
J96     (811)  ATTATTGGCGTGACTTTTGTTTATCAA
EC45    (811)  ATTATTGGCGTGACTTTTGTTTATCAA
B217    (811)  ATTATTGGCGTGACTTTTGTTTATCAA
DS17    (811)  ATTATTGGCGTGACTTTTGTTTATCAA
B212    (811)  ATTATTGGCGTGACTTTTGTTTATCAA
EC42    (811)  ATTATTGGCGTGACTTTTGTTTATCAA
EC56    (811)  ATTATTGGCGTGACTTTTGTTTATCAA
B210    (811)  ATTATTGGCGTGACTTTTGTTTATCAA
B203    (811)  ATTATTGGCGTGACTTTTGTTTATCAA
EC58    (811)  ATTATTGGCGTGACTTTTGTTTATCAA
EC60    (811)  ATTATTGCCGTGACTTTTGTTTATCAA
EC61    (811)  ATTATTGGCGTGACTTTTGTTTATCAA
EC80    (811)  ATTATTGGCGTGACTTTTGTTTATCAA
EC95    (811)  ATTATTGGCGTGACTTTTGTTTATCAA
EC62    (811)  ATTATTGGCGTGACTTTTGTTTATCAA
B238    (811)  ATTATTGCCGTGACTTTTGTTTATCAA
B240    (811)  ATTATTGGCGTGACTTTTGTTTATCAA
B242    (811)  ATTATTGGCGTGACTTTTGTTTATCAA
EC189   (811)  ATTATTGGCGTGACTTTTGTTTATCAA
```

Figure 2(a)

```
                    1                                                50
B210.aa       (1)   FACKTANGTAIPIGGGSANVYVNLAPVVNVGQNLVVDLSTQIFCHNDYPE
B212.aa       (1)   FACKTANGTAIPIGGGSANVYVNLAPAVNVGQNLVVDLSTQIFCHNDYPE
B217.aa       (1)   FACKTANGTAIPIGGGSANVYVNLAPAVNVGQNLVVDLSTQIFCHNDYPE
B223.aa       (1)   FACKTANGTAIPIGGGSANVYVNLAPAVNVGQNLVVDLSTQIFCHNDYPE
B228.aa       (1)   FACKTANGTAIPIGGGSANVYVNLAPAVNVGQNLVVDLSTQIFCHNDYPE
B238.aa       (1)   FACKTANGTAIPIGGGSANVYVNLAIAVNVGQNLVVDLSTQIFCHNDYPE
B240.aa       (1)   FACKTANGTAIPIGGGSANVYVNLAPVVNVGQNLVVDLSTQIFCHNDYPE
B242.aa       (1)   FACKTANGTAIPIGGGSANVYVNLAPAVNVGQNLVVDLSTQTFCHNDYPE
DS17.aa       (1)   FACKTANGTAIPIGGGSANVYVNLAPAVNVGQNLVVDLSTQIFCHNDYPE
EC42.aa       (1)   FACKTANGTAIPIGGGSANVYVNLAPAVNVGQNLVVDLSTQIFCHNDYPE
EC45.aa       (1)   FACKTANGTAIPIGGGSANVYVNLAPAVNVGQNLVVDLSTQIFCHNDYPE
EC56.aa       (1)   FACKTANGTAIPIGGGSANVYVNLAPVVNVGQNLVVDLSTQIFCHNDYPE
EC58.aa       (1)   FACKTANGTAIPIGGGSANVYVNLAPAVNVGQNLVVDLSTQIFCHNDYPE
EC60.aa       (1)   FACKTANGTAIPIGGGSANVYVNLAPVVNVGQNLVVDLSTQIFCHNDYPE
EC61.aa       (1)   FACKTANGTAIPIGGGSANVYVNLAPAVNVGQNLVVDLSTQIFCHNDYPE
EC62.aa       (1)   FACKTANGTAIPIGGGSANVYVNLAPAVNVGQNLVVDLSTQIFCHNDYPE
EC80.aa       (1)   FACKTANGTAIPIGGGSANVYVNLAPAVNVGQNLVVDLSTQIFCHNDYPE
EC89.aa       (1)   FACKTANGTAIPIGGGSANVYVNLAPAVNVGQNLVVDLSTQIFCHNDYPE
EC95.aa       (1)   FACKTANGTAIPIGGGSANVYVNLAPAVNVGQNLVVDLSTQIFCHNDYPE
G189.aa       (1)   FACKTANGTAIPIGGGSANVYVNLAPAVNVGQNLVVDLSTQIFCHNDYPE
J96.aa        (1)   FACKTANGTAIPIGGGSANVYVNLAPVVNVGQNLVVDLSTQIFCHNDYPE
NU14.aa       (1)   FACKTANGTAIPIGGGSANVYVNLAPAVNVGQNLVVDLSTQIFCHNDYPE
Consensus     (1)   FACKTANGTAIPIGGGSANVYVNLAPAVNVGQNLVVDLSTQIFCHNDYPE

                    51                                              100
B210.aa      (51)   TITDYVTLQRGSAYGGVLSNFSGIVKYSGSSYPFPTTSETPRVVYNSRTD
B212.aa      (51)   TITDYVTLQRGSAYGGVLSSFSGIVKYNGSSYPFPTTSETPRVVYNSRTD
B217.aa      (51)   TITDYVTLQRGAAYGGVLSSFSGTVKYNGSSYPFPTTSETPRVVYNSRTD
B223.aa      (51)   TITDYVTLQRGAAYGGVLSSFSGTVKYNGSSYPFPTTSETPRVVYNSRTD
B228.aa      (51)   TITDYVTLQRGSAYGGVLSNFSGTVKYSGSSYPFPTTSETPRVVYNSRTD
B238.aa      (51)   TITDYVTLQRGSAYGGVLSNFSGTVKYSGSSYPFPTTSETPRVVYNSRTD
B240.aa      (51)   TITDYVTLQRGSAYGGVLSNFSGTVKYSGSSYPFPTTSETPRVVYNSRTD
B242.aa      (51)   TITDYVTLQRGSAYGGVLSNFSGTVKYSGSSYPFPTTSETPRVVYNSRTD
DS17.aa      (51)   TITDYVTLQRGSAYGGVLSSFSGTVKYNGSSYPFPTTSETPRVVYNSRTD
EC42.aa      (51)   TITDYVTLQRGSAYGGVLSNFSGTVKYSGSSYPFPTTSETPRVVYNSRTD
EC45.aa      (51)   TITDYVTLQRGAAYGGVLSSFSGTVKYNGSSYPFPTTSETPRVVYNSRTD
EC56.aa      (51)   TITDYVTLQRGSAYGGVLSNFSGTVKYSGSSYPFPTTSETPRVVYNSRTD
EC58.aa      (51)   TITDYVTLQRGSAYGSVLSSFSGTVKYNGSSYPFPTTSETPRVVYNSRTD
EC60.aa      (51)   TITDYVTLQRGSAYGGVLSNFSGTVKYSGSSYPFPTTSETPRVVYNSRTD
EC61.aa      (51)   TITDYVTLQRGSAYGGVLSNFSGTVEYSGSSYPFPTTSETPRVVYNSRTD
EC62.aa      (51)   TITDYVTLQRGSAYGGVLSHFSGTVKYSGSSYPFPTTSETPRVVYNSRTD
EC80.aa      (51)   TITDYVTLQRGSAYGGVLSSFSGTVKYNGSSYPFPTTSETPRVVYNSRTD
EC89.aa      (51)   TITDYVTLQRGSAYGGVLSSFSGTVKYNGSSYPFPTTSETPRVVYNSRTD
EC95.aa      (51)   TITDYVTLQRGSAYGGVLSSFSGTVKYNGSSYPFPTTSETPRVVYNSRTD
G189.aa      (51)   TITDYVTLQRGSAYGGVLSNFSGTVKYSGSSYPFPTTSETPRVVYNSRTD
J96.aa       (51)   TITDYVTLQRGSAYGGVLSNFSGTVKYSGSSYPFPTTSETPRVVYNSRTD
NU14.aa      (51)   TITDYVTLQRGAAYGGVLSSFSGTVKYNGSSYPFPTTSETPRVVYNSRTD
Consensus    (51)   TITDYVTLQRGSAYGGVLSNFSGTVKYSGSSYPFPTTSETPRVVYNSRTD
```

Figure 2(b)

```
                     101                                               150
  B210.aa    (101)   KPWPVALYLTPVSSAGGVAIKAGSLIAVLILRQTNNYNSDDFQFVWNIYA
  B212.aa    (101)   KPWPVALYLTPVSSAGGVAIKAGSLIAVLILRQTNNYNSDDFQFVWNIYA
  B217.aa    (101)   KPWPVALYLTPVSSAGGVAIKAGSLIAVLILRQTNNYNSDDFQFVWNIYA
  B223.aa    (101)   KPWPVALYLTPVSSAGGVAIKAGSLIAVLILRQTNNYNSDDFQFVWNIYA
  B228.aa    (101)   KPWPVALYLTPVSSAGGVAIKAGSLIAVLILRQTNNYNSDDFQFVWNIYA
  B238.aa    (101)   KPWPVALYLTPVSSAGGVVIKAGSLIAVLILRQTNNYNSDDFQFVWNIYA
  B240.aa    (101)   KPWPVALYLTPVSSAGGLVIKAGSLIAVLILRQTNNYNSDDFQFVWNIYA
  B242.aa    (101)   KPWPVALYLTPVSSAGGVAIKAGSLIAVLILRQTNNYNSDDFQFVWNIYA
  DS17.aa    (101)   KPWPVALYLTPVSSAGGVAIKAGSLIAVLILRQTNNYNSDDFQFVWNIYA
  EC42.aa    (101)   KPWPVALYLTPVSSAGGVVIKAGSLIAVLILRQTNNYNSDDFQFVWNIYA
  EC45.aa    (101)   KPWPVALYLTPVSSAGGVAIKAGSLIAVLILRQTNNYNSDDFQFVWNIYA
  EC56.aa    (101)   KPWPVALYLTPVSSAGGVAIKAGSLIAVLILRQTNNYNSDDFQFVWNIYA
  EC58.aa    (101)   KPWPVALYLTPVSSAGGVAIKAGSLIAVLILRQTNNYNSDDFQFVWNIYA
  EC60.aa    (101)   KPWPVALYLTPVSSAGGVVIKAGSLIAVLILRQTNNYNSDDFQFVWNIYA
  EC61.aa    (101)   KPWPVALYLTPVSSAGGVAIKAGSLIAVLILRQTNNYNSDDFQFVWNIYA
  EC62.aa    (101)   KPWPVALYLTPVSSAGGVAIKAGSLMAVLILRQTNNYNSDDFQFVWNIYA
  EC80.aa    (101)   KPWPVALYLTPVSSAGGVAIKAGSLIAVLILRQTNNYNSDDFQFVWNIYA
  EC89.aa    (101)   KPWPVALYLTPVSSAGGVAIKAGSLIAVLILRQTNNYNSDDFQFVWNIYA
  EC95.aa    (101)   KPWPVALYLTLVSSAGGVAIKAGSLIAVLILRQTNNYNSDDFQFVWNIYA
  G189.aa    (101)   KPWPVALYLTPVSSAGGVAIKAGSLIAVLILRQTKNYNSDDFQFVWNIYA
   J96.aa    (101)   KPWPVALYLTPVSSAGGVAIKAGSLIAVLILRQTNNYNSDDFQFVWNIYA
  NU14.aa    (101)   KPWPVALYLTPVSSAGGVAIKAGSLIAVLILRQTNNYNSDDFQFVWNIYA
Consensus    (101)   KPWPVALYLTPVSSAGGVAIKAGSLIAVLILRQTNNYNSDDFQFVWNIYA
```

```
                     151                                               200
  B210.aa    (151)   NNDVVVPTGGCDASARDVTVTLPDYRGSVPIPLTVYCAKSQNLGYYLSGT
  B212.aa    (151)   NNDVVVPTGGCDASARDVTVTLPDYRGSVPIPLTVYCAKSQNLGYYLSGT
  B217.aa    (151)   NNDVVVPTGGCDVSARDVTVTLPDYRGSVPIPLTVYCAKSQNLGYYLSGT
  B223.aa    (151)   NNDVVVPTGGCDVSARDVTVTLPDYRGSVPIPLTVYCAKSQNLGYYLSGT
  B228.aa    (151)   NNDVVVPTGGCDVSAHDVTVTLPDYRGSVPIPLTVYCAKSQNLGYYLSGT
  B238.aa    (151)   NNDVVVPTGGCDVSARDVTVTLPDYRGSVPIPLTVYCAKSQNLGYYLSGT
  B240.aa    (151)   NNDVVVPTGGCDVSARDVTVTLPDYRGSVPIPLTVYCAKSQNLGYYLSGT
  B242.aa    (151)   NNDVVVPTGGCDVSAHDVTVTLPDYRGSVPIPLTVYCAKSQNLGYYLSGT
  DS17.aa    (151)   NNDVVVPTGGCDASARDVTVTLPDYRGSVPIPLTVYCAKSQNLGYYLSGT
  EC42.aa    (151)   NNDVVVPTGGCDVSARDVTVTLPDYPGSVPIPLTVYCAKSQNLGYYLSGT
  EC45.aa    (151)   NNDVVVPTGGCDVSARDVTVTLPDYPGSVPIPLTVYCAKSQNLGYYLSGT
  EC56.aa    (151)   NNDVVVPTGGCDVSARDVTVTLPDYPGSVPIPLTVYCAKSQNLGYYLSGT
  EC58.aa    (151)   NNDVVVPTGGCDVSARDVTVTLPDYRGSVPIPLTVYCAKSQNLGYYLSGT
  EC60.aa    (151)   NNDVVVPTGGCDVSARDVTVTLPDYRGSVPIPLTVYCAKSQNLGYYLSGT
  EC61.aa    (151)   NNDVVVPTGGCDVSARDVTVTLPDYRGSVPIPLTVYCAKSQNLGYYLSGT
  EC62.aa    (151)   NNDVVVPTGGCDVSARDVTVTLPDYRGSVPIPLTVYCAKSQNLGYYLSGT
  EC80.aa    (151)   NNDVVVPTGGCDVSARDVTVTLPDYRGSVPIPLTVYCAKSQNLGYYLSGT
  EC89.aa    (151)   NNDVVVPTGGCDVSARDVTVTLPDYRGSVPIPLTVYCAKSQNLGYYLSGT
  EC95.aa    (151)   NNDVVVPTGGCDVSARDVTVTLPDYRGSVPIPLTVYCAKSQNLGYYLSGT
  G189.aa    (151)   NNDVVVPTGGCDVSARDVTVTLPDYRGSVPIPLTVYCAKSQNLGYYLSGT
   J96.aa    (151)   NNDVVVPTGGCDVSARDVTVTLPDYPGSVPIPLTVYCAKSQNLGYYLSGT
  NU14.aa    (151)   NNDVVVPTGGCDVSARDVTVTLPDYRGSVPIPLTVYCAKSQNLGYYLSGT
Consensus    (151)   NNDVVVPTGGCDVSARDVTVTLPDYRGSVPIPLTVYCAKSQNLGYYLSGT
```

Figure 2(c)

```
                201                                                250
B210.aa   (201) HADAGNSIFTNTASFSPAQGVGVQLARNGTVIPANNTVSLGAVGTSAVSL
B212.aa   (201) HADAGNSIFTNTASFSPAQGVGVQLTRNGTIIPANNTVSLGAVGTSAVSL
B217.aa   (201) HADAGNSIFTNTASFSPAQGVGVQLTRNGTIIPANNTVSLGAVGTSAVSL
B223.aa   (201) HADAGNSIFTNTASFSPAQGVGVQLTRNGTIIPANNTVSLGAVGTSAVSL
B228.aa   (201) HADAGNSIFTNTASFSPAQGVGVQLTRNGTIIPANNTVSLGAVGTSAVSL
B238.aa   (201) HADAGNSIFTNTASFSPAQGVGVQLTRNGTIIPANNTVSLGAVGTSAVSL
B240.aa   (201) HADAGNSIFTNTASFSPAQGVGVQLTRNGTIIPTNNTVSLGAVGTSAVSL
B242.aa   (201) HADAGNSIFTNTASFSPAQGVGVQLTRNGTIIPANNTVSLGAVGTSAVSL
DS17.aa   (201) HADAGNSIFTNTASFSPAQGVGVQLTRNGTIIPANNTVSLGAVGTSAVSL
EC42.aa   (201) TADAGNSIFTNTASFSPAQGVGVQLTRNGTIIPANNTVSLGAVGTSAVSL
EC45.aa   (201) TADAGNSIFTNTASFSPAQGVGVQLTRNGTIIPANNTVSLGAVGTSAVSL
EC56.aa   (201) TADAGNSIFTNTASFSPAQGVGVQLTRNGTIIPANNTVSLGAVGTSAVSL
EC58.aa   (201) HADAGNSIFTNTASFSPAQGVGVQLTRNGTIIPANNTVSLGAVGTSAVSL
EC60.aa   (201) HADAGNSIFTNTASFSPAQGVGVQLTRNGTIIPANNTVSLGAVGTSAVSL
EC61.aa   (201) HADAGNSIFTNTASFSPAQGVGVQLTRNGTIIPANNTVSLGAVGTSAVSL
EC62.aa   (201) HADAGNSIFTNTASFSPAQGVGVQLTRNGTINPANNTVSLGAVGTSAVSL
EC80.aa   (201) HADAGNSIFTNTASFSPAQGVGVQLTANGTIVPANNTVSLGAVGTSAVSL
EC89.aa   (201) HADAGNSIFTNTASFSPAQGVGVQLTANGTIVPANNTVSLGAVGTSAVSL
EC95.aa   (201) HADAGNSIFTNTASFSPAQGVGVQLTRNGTIIPANNTVSLGAVGTSAVSL
G189.aa   (201) HADAGNSIFTNTASFSPAQGVGVQLTRNGTIIPANNTVSLGTVGTSAVSL
J96.aa    (201) TADAGNSIFTNTASFSPAQGVGVQLTRNGTIIPANNTVSLGAVGTSAVSL
NU14.aa   (201) HADAGNSIFTNTASFSPAQGVGVQLTRNGTIIPANNTVSLGAVGTSAVSL
Consensus (201) HADAGNSIFTNTASFSPAQGVGVQLTRNGTIIPANNTVSLGAVGTSAVSL
```

```
                251                         279
B210.aa   (251) GLTANYARTGGQVTAGNVQSIIGVTFVYQ
B212.aa   (251) GLTANYARTGGQVTAGNVQSIIGVTFVYQ
B217.aa   (251) GLTANYARTGGQVTAGNVQSIIGVTFVYQ
B223.aa   (251) GLTANYARTGGQVTAGNVQSIIGVTFVYQ
B228.aa   (251) GLTANYARTGGQVTAGNVQSIIGVTFVYQ
B238.aa   (251) GLTANYARTGGQVTAGNVQSIIGATFVYQ
B240.aa   (251) GLTANYARTGGQVTAGNVQSIIGVTFVYQ
B242.aa   (251) GLTANYARTGGQVTAGNVQSIIGVTFVYQ
DS17.aa   (251) GLTANYARTGGQVTAGNVQSIIGVTFVYQ
EC42.aa   (251) GLTANYARTGGQVTAGNVQSIIGVTFVYQ
EC45.aa   (251) GLTANYARTGGQVTAGNVQSIIGVTFVYQ
EC56.aa   (251) GLTANYARTGGQVTAGNVQSIIGVTFVYQ
EC58.aa   (251) GLTANYARTGGQVTAGNVQSIIGVTFVYQ
EC60.aa   (251) GLTANYARTGGQVTAGNVRSIIAVTFVYQ
EC61.aa   (251) GLTANYARTGGQVTAGNVQSIIGVTFVYQ
EC62.aa   (251) GLTANYARTGGQVTAGNVQSIIGVTFVYQ
EC80.aa   (251) GLTANYARTGGQVTAGNVQSIIGVTFVYQ
EC89.aa   (251) GLTANYARTGGQVTAGNVQSIIGVTFVYQ
EC95.aa   (251) GLTANYARTGGQVTAGNVQSIIGVTFVYQ
G189.aa   (251) GLTANYARTGGQVTAGNVQSIIGVTFVYQ
J96.aa    (251) GLTANYARTGGQVTAGNVQSIIGVTFVYQ
NU14.aa   (251) GLTANYARTGGQVTAGNVQSIIGVTFVYQ
Consensus (251) GLTANYARTGGQVTAGNVQSIIGVTFVYQ
```

Construction of pCGA101-8

Construction of pCGA122-30

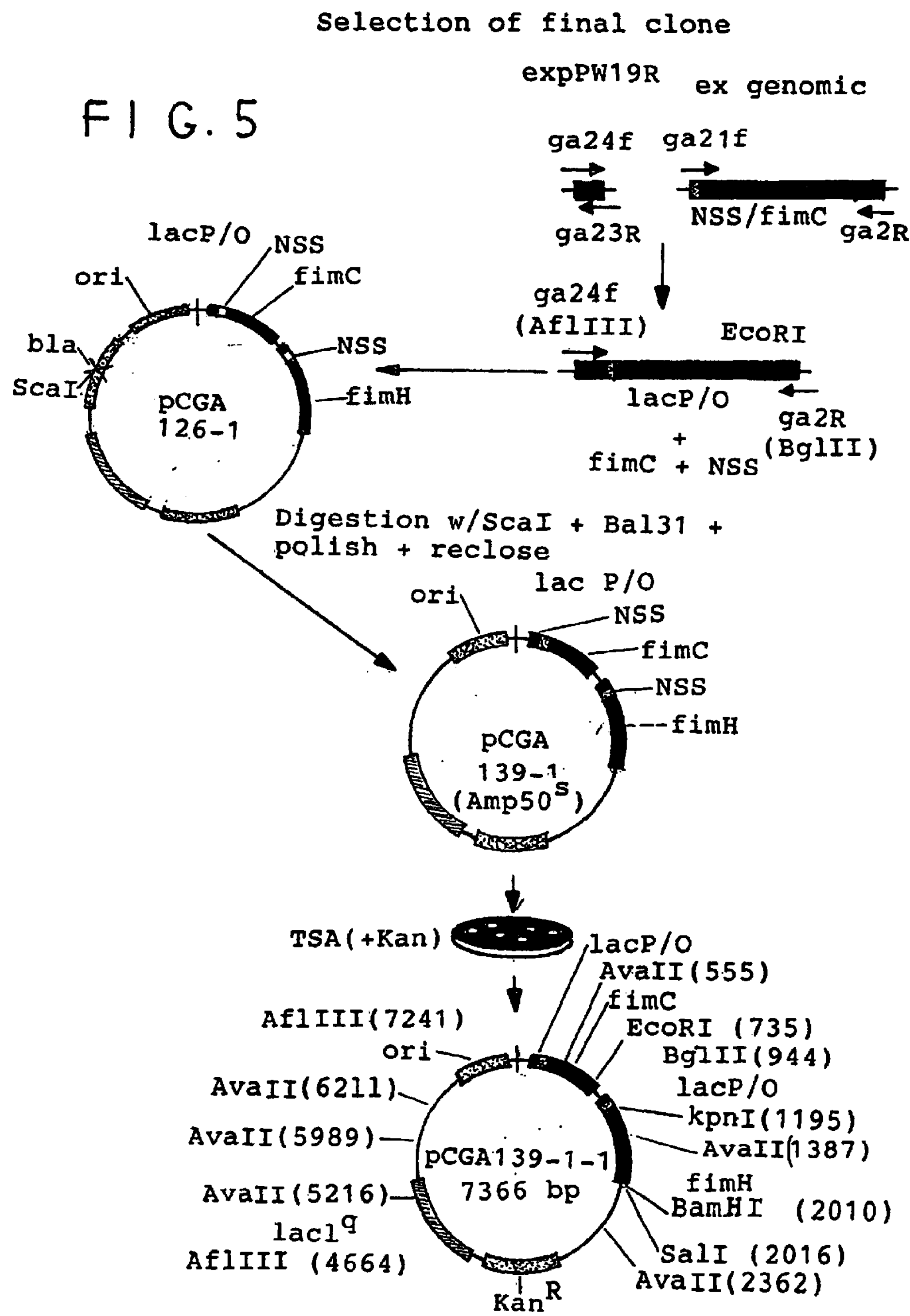

Selection of final clone
expPW19R
ex genomic
FIG. 5
ga24f
ga21f
ga23R
NSS/fimC
ga2R
lacP/O
NSS
ori
fimC
ga24f
(AflIII)
EcoRI
bla
NSS
ScaI
pCGA
126-1
fimH
lacP/O
ga2R
(BglII)
+
fimC + NSS
Digestion w/ScaI + Bal31 +
polish + reclose
ori
lac P/O
NSS
fimC
NSS
fimH
pCGA
139-1
(Amp50$^{S}$)
TSA(+Kan)
lacP/O
AvaII(555)
fimC
AflIII(7241)
EcoRI (735)
ori
BglII(944)
AvaII(6211)
lacP/O
kpnI(1195)
AvaII(5989)
AvaII(1387)
pCGA139-1-1
7366 bp
fimH
AvaII(5216)
BamHI (2010)
lacI$^{q}$
SalI (2016)
AflIII (4664)
AvaII(2362)
Kan$^{R}$

SEQUENCE LISTING

```
<160> NUMBER OF SEQ ID NOS: 64

<210> SEQ ID NO 1
<211> LENGTH: 837
<212> TYPE: DNA
<213> ORGANISM: E. coli

<400> SEQUENCE: 1

ttcgcctgta aaaccgccaa tggtaccgct atccctattg gcggtggcag cgccaatgtt      60

tatgtaaacc ttgcgcccgt cgtgaatgtg gggcaaaacc tggtcgtgga tctttcgacg     120

caaatctttt gccataacga ttatccggaa accattacag actatgtcac actgcaacga     180

ggctcggctt atggcggcgt gttatctaat ttttccggga tcgtaaaata tagtggcagt     240

agctatcctt tccctaccac cagcgaaacg ccgcgcgttg tttataattc gagaacggat     300

aagccgtggc cggtggcgct ttatttgacg cctgtgagca gtgcgggggg agtggcgatt     360

aaagcaggct cattaattgc cgtgcttatt ttgcgacaga ccaacaacta taacagcgat     420

ggtttccagt ttgtgtggaa tatttacgcc aataatgatg tggtggtgcc cactggcggc     480

tgcgatgctt ctgctcgtga tgtcaccgtt actctgccgg actaccctgg ttcagtgccg     540

attcctctta ccgtttattg tgcgaaaagc caaaacctgg ggtattacct ctccggcaca     600

accgcaggtg cgggcaactc gattttcacc aataccgcgt cgttttcacc cgcgcagggc     660

gtcggcgtac agttggcgcg caacggtacg gttattccag cgaataacac ggtatcgtta     720

ggagcagtag ggacttcggc ggtgagtctg ggattaacgg caaattacgc acgtaccgga     780

gggcaggtga ctgcagggaa tgtgcaatcg attattggcg tgacttttgt ttatcaa        837

<210> SEQ ID NO 2
<211> LENGTH: 837
<212> TYPE: DNA
<213> ORGANISM: E. coli

<400> SEQUENCE: 2

ttcgcctgta aaaccgccaa tggtaccgct atccctattg gcggtggcag cgccaatgtt      60

tatgtaaacc ttgcgcctgc cgtgaatgtg gggcaaaacc tggtcgtgga tctttcgacg     120

caaatctttt gccataacga ttacccggaa accattacag actatgtcac actgcaacga     180

ggttcggctt atggcggcgt gttatctagt ttttccggga tcgtaaaata taatggcagt     240

agctatcctt tccctactac cagcgaaacg ccgcgggttg tttataattc gagaacggat     300

aagccgtggc cggtggcgct ttatttgacg cctgtgagca gtgcgggggg agtggcgatt     360
```

-continued

```
aaagcaggct cattaattgc cgtgcttatt ttgcgacaga ccaacaacta taacagcgat    420

gatttccagt ttgtgtggaa tatttacgcc aataatgatg tggtggtgcc cactggcggc    480

tgcgatgctt ctgctcgtga tgtcaccgtt actctgccgg actaccctgg ttcagtgccg    540

attcctctta ccgtttattg tgcgaaaagc caaaacctgg ggtattacct ctccggcaca    600

accgcagatg cgggcaactc gattttcacc aataccgcgt cgttttcacc cgcgcagggc    660

gtcggcgtac agttgacgcg caacggtacg attattccag cgaataacac ggtatcgtta    720

ggagcagtag ggacttcggc ggtaagtctg ggattaacgg caaattacgc acgtaccgga    780

gggcaggtga ctgcagggaa tgtgcaatcg attattggcg tgacttttgt ttatcaa       837
```

```
<210> SEQ ID NO 3
<211> LENGTH: 837
<212> TYPE: DNA
<213> ORGANISM: E. coli

<400> SEQUENCE: 3

ttcgcctgta aaaccgccaa tggtacagct atccctattg gcggtggcag cgctaatgtt     60

tatgtaaacc ttgcgcctgc cgtgaatgtg gggcaaaacc tggtcgtaga tctttcgacg    120

caaatctttt gccataacga ttatccggaa accattacag actatgtcac actgcaacga    180

ggctcggctt atggcggcgt gttatctaat ttttccggga ccgtaaaata tagtggcagt    240

agctatccat ttccgaccac cagcgaaacg ccgcgggttg tttataattc gagaacggat    300

aagccgtggc cggtggcgct ttatttgacg cctgtgagca gtgcgggcgg ggtggcgatt    360

aaagctggct cattaattgc cgtgcttatt ttgcgacaga ccaacaacta taacagcgat    420

gatttccagt ttgtgtggaa tatttacgcc aataatgatg tggtggtgcc tactggcggc    480

tgcgatgttt ctgctcgtga tgtcaccgtt actctgccgg actaccctgg ttcagtgcca    540

attcctctta ccgtttattg tgcgaaaagc caaaacctgg ggtattacct ctccggcaca    600

accgcagatg cgggcaactc gattttcacc aataccgcgt cgttttcacc agcgcagggc    660

gtcggcgttc agttgacgcg caacggtacg attattccca cgaataacac ggtatcgtta    720

ggagcagtac ggacttcggc ggtaagtctg ggattaacgg caaattacgc acgtaccgga    780

gggcaggtga ctgcagggaa tgtgcaatcg attattggcg tgacttttgt ttatcaa       837
```

```
<210> SEQ ID NO 4
<211> LENGTH: 840
<212> TYPE: DNA
<213> ORGANISM: E. coli

<400> SEQUENCE: 4

ttcgcctgta aaaccgccaa tggtaccgca atccctattg gcggtggcag cgccaatgtt     60

tatgtaaacc ttgcgcctgc cgtgaatgtg gggcaaaacc tggtcgtaga tctttcgacg    120

caaatctttt gccataacga ttacccagaa accattacag actatgtcac actgcaacga    180

ggtgcggctt atggcggcgt gttatctagt ttttccggga ccgtaaaata taatggcagt    240

agctatcctt tccctactac cagcgaaacg ccgcgggttg tttataattc gagaacggat    300

aagccgtggc cggtggcgct ttatttgacg ccggtgagca gtgcgggggg agtggcgatt    360

aaagctggct cattaattgc cgtgcttatt ttgcgacaga ccaacaacta taacagcgat    420

gatttccagt ttgtgtggaa tatttacgcc aataatgatg tggtggtgcc cactggcggc    480

tgcgatgttt ctgctcgtga tgtcaccgtt actctgccgg actaccctgg ttcagtgccg    540
```

-continued

```
attcctctta ccgtttattg tgcgaaaagc caaaacctgg ggtattacct ctccggcaca    600

accgcagatg cgggcaactc gattttcacc aataccgcgt cgttttcacc cgcgcagggc    660

gtcggcgtac agttgacgcg caacggtacg attattccag cgaataacac ggtatcgtta    720

ggagcagtag ggacttcggc ggtaagtctg ggattaacgg caaattacgc acgtaccgga    780

gggcaggtga ctgcagggaa tgtgcaatcg attattggcg tgacttttgt ttatcaataa    840
```

<210> SEQ ID NO 5
<211> LENGTH: 840
<212> TYPE: DNA
<213> ORGANISM: E. coli

<400> SEQUENCE: 5

```
ttcgcctgta aaaccgccaa tggtaccgct attcctattg gcggtggcag cgctaatgtt     60

tatgtaaacc ttgcgcctgc cgtgaatgtg gggcaaaacc tggtcgtaga tctttcgacg    120

caaatctttt gccataacga ttatccggaa accattacag actatgtcac actgcaacga    180

ggctcggctt atggcggcgt gttatctaat tttttccggga ccgtaaaata tagtggcagt   240

agctatccat ttccgactac cagcgaaacg ccgcgggttg tttataattc gagaacggat    300

aagccgtggc cggtggcgct ttatttgacg cctgtgagca gtgcgggtgg ggtggcgatt    360

aaagctggct cattaattgc cgtgcttatt ttgcgacaga ccaacaacta taacagcgat    420

gatttccagt ttgtgtggaa tatttacgcc aataatgatg tggtggtgcc tactggcggc    480

tgcgatgttt ctgctcatga tgtcaccgtt actctgccgg actaccctgg ttcagtgcca    540

attcctctta ccgtttattg tgcgaaaagc caaaacctgg ggtattacct ctccggcaca    600

accgcagatg cgggcaactc gattttcacc aataccgcgt cgttttcacc agcgcagggc    660

gtcggcgtac agttgacgcg caacggtacg attattccag cgaataacac ggtatcgtta    720

ggagcagtag ggacttcggc ggtaagtctg ggattaacgg caaattacgc acgtaccgga    780

gggcaggtga ctgcagggaa tgtgcaatcg attattggcg tgacttttgt ttatcaataa    840
```

<210> SEQ ID NO 6
<211> LENGTH: 837
<212> TYPE: DNA
<213> ORGANISM: E. coli

<400> SEQUENCE: 6

```
ttcgcctgta aaaccgccaa tggcaccgct atccctattg gcggtggcag cgccaatgtt     60

tatgtaaaca ttgcgcccgc cgtgaatgtg gggcaaaacc tggtcgtgga tctttcgacg    120

caaatctttt gccataacga ttacccggaa accattacag attatgtcac actgcaacga    180

ggctcggctt atggcggcgt gttatctaat tttttccggga ccgtaaaata tagtggcagt   240

agctatccat ttccgaccac cagtgaaacg ccgcgggttg tttataattc gagaacggat    300

aagccgtggc cggtggcgct ttatttgacg cctgtgagca gtgcgggcgg ggtggtgatt    360

aaagctggct cattaattgc cgtgcttatt ttgcgacaga ccaacaacta taacagcgat    420

gatttccagt ttgtgtggaa tatttacgcc aataatgatg tggtggtgcc cactggcggc    480

tgcgatgttt ctgctcgtga tgtcaccgtt actctgccgg actaccctgg ttcagtgccg    540

attcctctta ccgtttattg tgcgaaaagc caaaacctgg ggtattacct ctccggcaca    600

accgcagatg cgggcaactc gattttcacc aataccgcgt cgttttcacc tgcacagggc    660

gtcggcgtac agttgacgcg caacggtacg attattccag cgaataacac ggtatcgtta    720

ggagcagtag ggacttcggc ggtaagtctg ggattaacgg caaattacgc acgtaccgga    780
```

-continued

```
gggcaggtga ctgcagggaa tgtgcaatcg attattgccg tgacttttgt ttatcaa       837


<210> SEQ ID NO 7
<211> LENGTH: 837
<212> TYPE: DNA
<213> ORGANISM: E. coli

<400> SEQUENCE: 7

ttcgcctgta aaaccgccaa tggtaccgct atccctattg gcggtggcag cgccaatgtt     60

tatgtaaacc ttgcgcccgt cgtgaatgtg gggcaaaacc tggtcgtgga tctttcgacg    120

caaatctttt gccataacga ttatccggaa accattacag actatgtcac actgcaacga    180

ggctcggctt atggcggcgt gttatctaat ttttccggga ccgtaaaata tagtggcagt    240

agctatccat ttcctaccac cagcgaaacg ccgcgcgttg tttataattc gagaacggat    300

aagccgtggc cggtggcgct ttatttgacg cctgtgagca gtgcgggcgg gttggtgatt    360

aaagctggct cattaattgc cgtgcttatt ttgcgacaga ccaacaacta taacagcgat    420

gatttccagt ttgtgtggaa tatttacgcc aataatgatg tggtggtgcc tactggcggc    480

tgcgatgttt ctgctcgtga tgtcaccgtt actctgccgg actaccgtgg ttcagtgcca    540

attcctctta ccgtttattg tgcgaaaagc caaaacctgg ggtattacct ctccggcaca    600

accgcagatg cgggcaactc gattttcacc aataccgcgt cgttttcacc tgcacagggc    660

gtcggcgtac agttgacgcg caacggtacg attattccaa cgaataacac ggtatcgtta    720

ggagcagtag ggacttcggc ggtaagtctg ggattaacgg caaattacgc acgtaccgga    780

gggcaggtga ctgcagggaa tgtgcaatcg attattggcg tgacttttgt ttatcaa       837


<210> SEQ ID NO 8
<211> LENGTH: 837
<212> TYPE: DNA
<213> ORGANISM: E. coli

<400> SEQUENCE: 8

tttgcctgta aaaccgccaa tggcaccgct atccctattg gcggtggcag cgccaatgtt     60

tatgtaaact tggcgcccgc cgtgaatgtg gggcaaaacc tggtcgtgga tctttcgacg    120

caaacctttt gccataacga ttatccggaa accattacag actatgtcac actgcaacga    180

ggctcggctt atggcggcgt gttatctaat ttttccggga ccgtaaaata tagtggcagt    240

agctatccat ttccgactac cagcgaaacg ccgcgggttg tttataattc gagaacggat    300

aagccgtggc cggtggcgct ttatttgacg cctgtgagca gtgcgggtgg ggtggcgatt    360

aaagctggct cattaattgc cgtgcttatt ttgcgacaga ccaacaacta taacagcgat    420

gatttccagt ttgtgtggaa tatttacgcc aataatgatg tggtggtgcc tactggcggc    480

tgcgatgttt ctgctcatga tgtcaccgtt actctgccgg actaccctgg ttcagtgcca    540

attcctctta ccgtttattg tgcgaaaagc caaaacctgg ggtattacct ctccggcaca    600

accgcagatg cgggcaactc gattttcacc aataccgcgt cgttttcacc agcgcagggc    660

gtcggcgtac agttgacgcg caacggtacg attattccag cgaataacac ggtatcgtta    720

ggagcagtag ggacttcggc ggtgagtctg ggattaacgg caaattacgc acgtaccgga    780

gggcaggtga ctgcagggaa tgtgcaatcg attattggcg tgacttttgt ttatcaa       837


<210> SEQ ID NO 9
<211> LENGTH: 837
<212> TYPE: DNA
```

-continued

<213> ORGANISM: E. coli

<400> SEQUENCE: 9

```
ttcgcctgta aaaccgccaa tggtaccgca atccctattg gcggtggcag cgccaatgtt     60

tatgtaaacc ttgcgcctgc cgtgaatgtg gggcaaaacc tggtcgtaga tctttcgacg    120

caaatctttt gccataacga ttacccagaa accattacag actatgtcac actgcaacga    180

ggttcggctt atggcggcgt gttatctagt ttttccggga ccgtaaaata taatggcagt    240

agctatcctt tccctactac cagcgaaacg ccgcgggttg tttataattc gagaacggat    300

aagccgtggc cggtggcgct ttatttgacg ccggtgagca gtgcgggggg agtggcgatt    360

aaagctggct cattaattgc cgtgcttatt ttgcgacaga ccaacaacta taacagcgat    420

gatttccagt ttgtgtggaa tatttacgcc aataatgatg tggtggtgcc cactggcggc    480

tgtgatgctt ctgctcgtga tgtcaccgtt actttgccgg actaccctgg ttcagtgccg    540

attcctctta ccgtttattg tgcgaaaagc caaaacctgg ggtattacct atccggcaca    600

accgcagatg cgggcaactc gattttcacc aataccgcgt cgttttcacc cgcgcagggc    660

gtcggcgtac agttgacgcg caacggtacg attattccag cgaataacac ggtatcgtta    720

ggagcagtag ggacttcggc ggtaagtctg ggattaacgg caaattacgc acgtaccgga    780

gggcaggtga ctgcagggaa tgtgcaatcg attattggcg tgacttttgt ttatcaa       837
```

<210> SEQ ID NO 10
<211> LENGTH: 840
<212> TYPE: DNA
<213> ORGANISM: E. coli

<400> SEQUENCE: 10

```
ttcgcctgta aaaccgccaa tggcaccgct atccctattg gcggtggcag cgccaatgtt     60

tatgtaaacc ttgcgcccgc cgtgaatgtg gggcaaaacc tggtcgtgga tctttcgacg    120

caaatctttt gccataacga ttacccggaa accattacag attatgtcac actgcaacga    180

ggctcggctt atggcggcgt gttatctaat ttttccggga ccgtaaaata tagtggcagt    240

agctatccat ttccgaccac cagtgaaacg ccgcgggttg tttataattc gagaacggat    300

aagccgtggc cggtggcgct ttatttgacg cctgtgagca gtgcgggcgg ggtggtgatt    360

aaagctggct cattaattgc cgtgcttatt ttgcgacaga ccaacaacta taacagcgat    420

gatttccagt ttgtgtggaa tatttacgcc aataatgatg tggtggtgcc cactggcggc    480

tgcgatgttt ctgctcgtga tgtcaccgtt actctgccgg actaccctgg ttcagtgccg    540

attcctctta ccgtttattg tgcgaaaagc caaaacctgg ggtattacct ctccggcaca    600

accgcagatg cgggcaactc gattttcacc aataccgcgt cgttttcacc tgcacagggc    660

gtcggcgtac agttgacgcg caacggtacg attattccag cgaataacac ggtatcgtta    720

ggagcagtag ggacttcggc ggtaagtctg ggattaacgg caaattacgc acgtaccgga    780

gggcaggtga ctgcagggaa tgtgcaatcg attattggcg tgacttttgt ttatcaataa    840
```

<210> SEQ ID NO 11
<211> LENGTH: 837
<212> TYPE: DNA
<213> ORGANISM: E. coli

<400> SEQUENCE: 11

```
ttcgcctgta aaaccgccaa tggtaccgca atccctattg gcggtggcag cgccaatgtt     60

tatgtaaacc ttgcgcctgc cgtgaatgtg gggcaaaacc tggtcgtaga tctttcgacg    120
```

-continued

```
caaatctttt gccataacga ttacccagaa accattacag actatgtcac actgcaacga    180
ggtgcggctt atggcggcgt gttatctagt ttttccggga ccgtaaaata taatggcagt    240
agctatcctt tccctactac cagcgaaacg ccgcgggttg tttataattc gagaacggat    300
aagccgtggc cggtggcgct ttatttgacg ccggtgagca gtgcgggggg agtggcgatt    360
aaagctggct cattaattgc cgtgcttatt ttgcgacaga ccaacaacta taacagcgat    420
gatttccagt ttgtgtggaa tatttacgcc aataatgatg tggtggtgcc cactggcggc    480
tgcgatgttt ctgctcgtga tgtcaccgtt actctgccgg actaccctgg ttcagtgccg    540
attcctctta ccgtttattg tgcgaaaagc caaaacctgg ggtattacct ctccggcaca    600
accgcagatg cgggcaactc gattttcacc aataccgcgt cgttttcacc cgcgcagggc    660
gtcggcgtac agttgacgcg caacggtacg attattccag cgaataacac ggtatcgtta    720
ggagcagtag ggacttcggc ggtaagtctg ggattaacgg caaattacgc acgtaccgga    780
gggcaggtga ctgcagggaa tgtgcaatcg attattggcg tgacttttgt ttatcaa       837
```

<210> SEQ ID NO 12
<211> LENGTH: 840
<212> TYPE: DNA
<213> ORGANISM: E. coli

<400> SEQUENCE: 12

```
ttcgcctgta aaaccgccaa tggtaccgct atccctattg gcggtggcag cgccaatgtt     60
tatgtaaacc ttgcgcccgt cgtgaatgtg gggcaaaacc tggtcgtgga tctttcgacg    120
caaatctttt gccataacga ttatccggaa accattacag actatgtcac actgcaacga    180
ggctcggctt atggcggcgt gttatctaat ttttccggga ccgtaaaata tagtggcagt    240
agctatccat ttcctaccac cagcgaaacg ccgcgcgttg tttataattc gagaacggat    300
aagccgtggc cggtggcgct ttatttgacg cctgtgagca gtgcgggcgg ggtggcgatt    360
aaagctggct cattaattgc cgtgcttatt ttgcgacaga ccaacaacta taacagcgat    420
gatttccagt ttgtgtggaa tatttacgcc aataatgatg tggtggtgcc tactggcggc    480
tgcgatgttt ctgctcgtga tgtcaccgtt actctgccgg actaccctgg ttcagtgcca    540
attcctctta ccgtttattg tgcgaaaagc caaaacctgg ggtattacct ctccggcaca    600
accgcagatg cgggcaactc gattttcacc aataccgcgt cgttttcacc tgcacagggc    660
gtcggcgtac agttgacgcg caacggtacg attattccag cgaataacac ggtatcgtta    720
ggagcagtag ggacttcggc ggtgagtctg ggattaacgg caaattatgc acgtaccgga    780
gggcaggtga ctgcagggaa tgtgcaatcg attattggcg tgacttttgt ttatcaataa    840
```

<210> SEQ ID NO 13
<211> LENGTH: 837
<212> TYPE: DNA
<213> ORGANISM: E. coli

<400> SEQUENCE: 13

```
ttcgcctgta aaaccgccaa tggtaccgca atccctattg gcggtggcag cgccaatgtt     60
tatgtaaacc ttgcgcctgc cgtgaatgtg gggcaaaacc tggtcgtaga tctttcgacg    120
caaatctttt gccataacga ttacccagaa accattacag actatgtcac actgcaacga    180
ggttcggctt atggcagcgt gttatctagt ttttccggga ccgtaaaata taatggcagt    240
agctatcctt tccctactac cagcgaaacg ccgcgggttg tttataattc gagaacggat    300
```

-continued

```
aagccgtggc cggtggcgct ttatttgacg ccggtgagca gtgcgggggg agtggcgatt    360

aaagctggct cattaattgc cgtgcttatt ttgcgacaga ccaacaacta taacagcgat    420

gatttccagt ttgtgtggaa tatttacgcc aataatgatg tggtggtgcc cactggcggc    480

tgtgatgttt ctgctcgtga tgtcaccgtt actctgccgg actaccctgg ttcagtgccg    540

attcctctta ccgtttattg tgcgaaaagc caaaacctgg ggtattacct atccggcaca    600

accgcagatg cgggcaactc gattttcacc aataccgcgt cgttttcacc cgcgcagggc    660

gtcggcgtac agttgacgcg caacggtacg attattccag cgaataacac ggtatcgtta    720

ggagcagtag ggacttcggc ggtaagtctg ggattaacgg caaattacgc acgtaccgga    780

gggcaggtga ctgcagggaa tgtgcaatcg attattggcg tgacttttgt ttatcaa       837


<210> SEQ ID NO 14
<211> LENGTH: 837
<212> TYPE: DNA
<213> ORGANISM: E. coli

<400> SEQUENCE: 14

ttcgcctgta aaaccgccaa tggtaccgca atccctattg gcggtggcag cgccaatgtt     60

tatgtaaacc ttgcgcctgc cgtgaatgtg gggcaaaacc tggtcgtaga tctttcgacg    120

caaatctttt gccataacga ttacccagaa accattacag actatgtcac actgcaacga    180

ggttcggctt atggcagcgt gttatctagt ttttccggga ccgtaaaata taatggcagt    240

agctatcctt tccctactac cagcgaaacg ccgcgggttg tttataattc gagaacggat    300

aagccgtggc cggtggcgct ttatttgacg ccggtgagca gtgcgggggg agtggcgatt    360

aaagctggct cattaattgc cgtgcttatt ttgcgacaga ccaacaacta taacagcgat    420

gatttccagt ttgtgtggaa tatttacgcc aataatgatg tggtggtgcc cactggcggc    480

tgtgatgttt ctgctcgtga tgtcaccgtt actctgccgg actaccctgg ttcagtgccg    540

attcctctta ccgtttattg tgcgaaaagc caaaacctgg ggtattacct atccggcaca    600

accgcagatg cgggcaactc gattttcacc aataccgcgt cgttttcacc cgcgcagggc    660

gtcggcgtac agttgacgcg caacggtacg attattccag cgaataacac ggtatcgtta    720

ggagcagtag ggacttcggc ggtaagtctg ggattaacgg caaattacgc acgtaccgga    780

gggcaggtga ctgcagggaa tgtgcaatcg attattggcg tgacttttgt ttatcaa       837


<210> SEQ ID NO 15
<211> LENGTH: 837
<212> TYPE: DNA
<213> ORGANISM: E. coli

<400> SEQUENCE: 15

ttcgcctata aaaccgccaa tggtaccgct atccctattg gcggtggcag cgccaatgtt     60

tatgtaaacc ttgcgcccgc cgtgaatgtg gggcaaaacc tggtcgtgga tctttcgacg    120

caaatctttt gccataacga ttatccggaa accattacag actatgtcac actgcaacga    180

ggctcggctt atggcggcgt gttatctaat ttttccggga ccgtagaata tagtggcagt    240

agctatccat ttcctaccac cagcgaaacg ccgcgcgttg tttataattc gagaacggat    300

aagccgtggc cggtggcgct ttatttgacg cctgtgagca gtgcgggcgg ggtggcgatt    360

aaagctggct cattaattgc cgtgcttatt ttgcgacaga ccaacaacta taacagcgat    420

gatttccagt ttgtgtggaa tatttacgcc aataatgatg tggtggtgcc tactggcggc    480

tgcgatgttt ctgctcgtga tgtcaccgtt actctgccgg actaccctgg ttcagtgcca    540
```

```
attcctctta ccgtttattg tgcgaaaagc caaaacctgg ggtattacct ctccggcaca    600

accgcagatg cgggcaactc gattttcacc aataccgcgt cgttttcacc tgcacagggc    660

gtcggcgtac agttgacgcg caacggtacg attattccag cgaataacac ggtatcttta    720

ggagcagtag ggacttcggc ggtgagtctg ggattaacgg caaattatgc acgtaccgga    780

gggcaggtga ctgcagggaa tgtgcaatcg attattggcg tgacttttgt ttatcaa       837
```

<210> SEQ ID NO 16
<211> LENGTH: 837
<212> TYPE: DNA
<213> ORGANISM: E. coli

<400> SEQUENCE: 16

```
atcgcctgta aaaccgccaa tggcaccgct atccctattg gcggtggcag cgccaatgtt     60

tatgtaaacc ttgcgcccgc cgtgaatgtg ggcaaaaacc tggtcgtaga tctttcgacg    120

caaatctttt gccataacga ttacccggaa accattacag actatgtcac actgcaacga    180

ggttcggctt atggcggcgt gttatctcat ttttccggga ccgtaaaata tagtggcagt    240

agctatccat ttcctaccac cagcgaaacg ccgcgcgttg tttataattc gagaacggat    300

aagccgtggc cggtggcgct ttatttgacg cctgtgagca gtgcgggtgg ggtggcgatt    360

aaggctggct cattaatggc tgtgctaatt ttgcgacaga ccaataacta taacagcgat    420

gatttccagt ttgtgtggaa tatttacgcc aataatgatg tggtggtgcc cactggcggc    480

tgtgatgttt ctgctcgtga tgtcaccgtt actctgccag actaccctgg ttcagtgccg    540

attcctctta ccgtttattg tgcgaaaagc caaaacctgg ggtattacct ctccggcaca    600

accgcagatg cgggcaactc gattttcacc aataccgcgt cgttttcacc tgcacagggc    660

gtcggcgtac agttaacgcg caacggtacg attaatccag cgaataacac ggtatcgtta    720

ggagcagtag ggacttcggc ggtaagtctg ggattaacgg caaattacgc acgtaccgga    780

gggcaggtga ctgcagggaa tgtgcaatcg attattggcg tgacttttgt ttatcaa       837
```

<210> SEQ ID NO 17
<211> LENGTH: 837
<212> TYPE: DNA
<213> ORGANISM: E. coli

<400> SEQUENCE: 17

```
ttcgcctgta aaaccgccaa tggtaccgct atccctattg gcggtggcag cgccaatgtt     60

tatgtaaacc ttgcgcccgt cgtgaatgtg ggcaaaaacc tggtcgtgga tctttcgacg    120

caaatctttt gccataacga ttatccggaa accattacag actatgtcac actgcaacga    180

ggctcggctt atggcggcgt gttatctaat ttttccggga ccgtaaaata tagtggcagt    240

agctatccat ttcctaccac cagcgaaacg ccgcgcgttg tttataattc gagaacggat    300

aagccgtggc cggtggcgct ttatttgacg cctgtgagca gtgcgggcgg ggtggcgatt    360

aaagctggct cattaattgc cgtgcttatt ttgcgacaga ccaacaacta taacagcgat    420

gatttccagt ttgtgtggaa tatttacgcc aataatgatg tggtggtgcc tactggcggc    480

tgcgatgttt ctgctcgtga tgtcaccgtt actctgccgg actaccgtgg ttcagtgcca    540

attcctctta ccgtttattg tgcgaaaagc caaaacctgg ggtattacct ctccggcaca    600

cacgcagatg cgggcaactc gattttcacc aataccgcgt cgttttcacc tgcacagggc    660

gtcggcgtac agttgacgcg caacggtacg attattccag cgaataacac ggtatcgtta    720
```

-continued

```
ggagcagtag ggacttcggc ggtgagtctg ggattaacgg caaattatgc acgtaccgga    780

gggcaggtga ctgcagggaa tgtgcaatcg attattggcg tgacttttgt ttatcaa       837


<210> SEQ ID NO 18
<211> LENGTH: 837
<212> TYPE: DNA
<213> ORGANISM: E. coli

<400> SEQUENCE: 18

ttcgcctgta aaaccgccaa tggtaccgct atccctattg gcggtggcag cgccaatgtt     60

tatgtaaacc ttgcgcctgc cgtgaatgtg gggcaaaacc tggtcgtgga tctttcgacg    120

caaatctttt gccataacga ttacccggaa accattacag actatgtcac actgcaacga    180

ggttcggctt atggcggcgt gttatctagt ttttccggga ccgtaaaata taatggcagt    240

agctatcctt tccctactac cagcgaaacg ccgcgggttg tttataattc gagaacggat    300

aagccgtggc cggtggcgct ttatttgacg cctgtgagca gtgcgggggg agtggcgatt    360

aaagctggct cattaattgc cgtgcttatt ttgcgacaga ccaacaacta taacagcgat    420

gatttccagt ttgtgtggaa tatttacgcc aataatgatg tggtggtgcc cactggcggc    480

tgcgatgttt ctgctcgtga tgtcaccgtt actctgccgg actaccctgg ttcagtgccg    540

attcctctta ccgtttattg tgcgaaaagc caaaacctgg ggtattacct ctccggcaca    600

accgcagatg cgggcaactc gattttcacc aataccgcgt cgttttcacc cgcgcagggc    660

gtcggcgtac agttggcgcg caacggtacg gttattccag cgaataacac ggtatcgtta    720

ggagcagtag ggacttcggc ggtaagtctg ggattaacgg caaattacgc acgtaccgga    780

gggcaggtga ctgcagggaa tgtgcaatcg attattggcg tgacttttgt ttatcaa       837


<210> SEQ ID NO 19
<211> LENGTH: 837
<212> TYPE: DNA
<213> ORGANISM: E. coli

<400> SEQUENCE: 19

ttcgcctgta aaaccgccaa tggtaccgca atccctattg gcggtggcag cgccaatgtt     60

tatgtaaacc ttgcgcctgc cgtgaatgtg gggcaaaacc tggtcgtaga tctttcgacg    120

caaatctttt gccataacga ttacccagaa accattacag actatgtcac actgcaacga    180

ggttcggctt atggcggcgt gttatctagt ttttccggga ccgtaaaata taatggcagt    240

agctatcctt tccctactac cagcgaaacg ccgcgggttg tttataattc gagaacggat    300

aagccgtggc cggtggcgct ttatttgacg ctggtgagca gtgcgggggg agtggcgatt    360

aaagctggct cattaattgc cgtgcttatt ttgcgacaga ccaacaacta taacagcgat    420

gatttccagt ttgtgtggaa tatttacgcc aataatgatg tggtggtgcc cactggcggc    480

tgtgatgttt ctgctcgtga tgtcaccgtt actctgccgg actaccctgg ttcagtgccg    540

attcctctta ccgtttattg tgcgaaaagc caaaacctgg ggtattacct atccggcaca    600

accgcagatg cgggcaactc gattttcacc aataccgcgt cgttttcacc cgcgcagggc    660

gtcggcgtac agttgacgcg caacggtacg attattccag cgaataacac ggtatcgtta    720

ggagcagtag ggacttcggc ggtaagtctg ggattaacgg caaattacgc acgtaccgga    780

gggcaggtga ctgcagggaa tgtgcaatcg attattggcg tgacttttgt ttatcaa       837


<210> SEQ ID NO 20
<211> LENGTH: 837
```

-continued

<212> TYPE: DNA
<213> ORGANISM: E. coli

<400> SEQUENCE: 20
ttcgcctgta aaaccgccaa tggtaccgct atccctattg gcggtggcag cgctaatgtt 60
tatgtaaacc ttgcgcctgc cgtgaatgtg gggcaaaacc tggtcgtaga tctttcgacg 120
caaatctttt gccataacga ttatccggaa accattacag actatgtcac actgcaacga 180
ggctcggctt atggcggcgt gttatctaat ttttccggga ccgtaaaata tagtggcagt 240
agctatccat ttccgaccac cagcgaaacg ccgcgggttg tttataattc gagaacggat 300
aagccgtggc cggtggcgct ttatttgacg cctgtgagca gtgcgggcgg ggtggcgatt 360
aaagctggct cattaattgc cgtgcttatt ttgcgacaga ccaaaaacta taacagcgat 420
gatttccagt ttgtgtggaa tatttacgcc aataatgatg tggtagtgcc tactggcggc 480
tgcgatgttt ctgctcgtga tgtcaccgtt actctgccgg actaccctgg ttcagtgcca 540
attcctctta ccgtttattg tgcgaaaagc caaaacctgg ggtattacct ctccggcaca 600
accgcagatg cgggcaactc gattttcacc aataccgcgt cgttttcacc agcgcagggc 660
gtcggcgtac agttgacgcg caacggtacg attattccag cgaataacac ggtatcgtta 720
ggaacagtag gaacttcggc ggtaagtctg ggattaacgg caaattacgc acgtaccggc 780
gggcaggtga ctgcagggaa tgtgcaatcg attattggcg tgacttttgt ttatcaa 837

<210> SEQ ID NO 21
<211> LENGTH: 837
<212> TYPE: DNA
<213> ORGANISM: E. coli

<400> SEQUENCE: 21
ttcgcctgta aaaccgccaa tggtaccgct atccctattg gcggtggcag cgccaatgtt 60
tatgtaaacc ttgcgcccgt cgtgaatgtg gggcaaaacc tggtcgtgga tctttcgacg 120
caaatctttt gccataacga ttatccggaa accattacag actatgtcac actgcaacga 180
ggctcggctt atggcggcgt gttatctaat ttttccggga ccgtaaaata tagtggcagt 240
agctatccat ttcctaccac cagcgaaacg ccgcgcgttg tttataattc gagaacggat 300
aagccgtggc cggtggcgct ttatttgacg cctgtgagca gtgcgggcgg ggtggcgatt 360
aaagctggct cattaattgc cgtgcttatt ttgcgacaga ccaacaacta taacagcgat 420
gatttccagt ttgtgtggaa tatttacgcc aataatgatg tggtggtgcc tactggcggc 480
tgcgatgttt ctgctcgtga tgtcaccgtt actctgccgg actaccctgg ttcagtgcca 540
attcctctta ccgtttattg tgcgaaaagc caaaacctgg ggtattacct ctccggcaca 600
accgcagatg cgggcaactc gattttcacc aataccgcgt cgttttcacc tgcacagggc 660
gtcggcgtac agttgacgcg caacggtacg attattccag cgaataacac ggtatcgtta 720
ggagcagtag ggacttcggc ggtgagtctg ggattaacgg caaattatgc acgtaccgga 780
gggcaggtga ctgcagggaa tgtgcaatcg attattggcg tgacttttgt ttatcaa 837

<210> SEQ ID NO 22
<211> LENGTH: 837
<212> TYPE: DNA
<213> ORGANISM: E. coli

<400> SEQUENCE: 22
ttcgcctgta aaaccgccaa tggtaccgca atccctattg gcggtggcag cgccaatgtt 60

-continued

```
tatgtaaacc ttgcgcctgc cgtgaatgtg gggcaaaacc tggtcgtaga tctttcgacg    120

caaatctttt gccataacga ttacccagaa accattacag actatgtcac actgcaacga    180

ggtgcggctt atggcggcgt gttatctagt ttttccggga ccgtaaaata taatggcagt    240

agctatcctt tccctactac cagcgaaacg ccgcgggttg tttataattc gagaacggat    300

aagccgtggc cggtggcgct ttatttgacg ccggtgagca gtgcgggggg agtggcgatt    360

aaagctggct cattaattgc cgtgcttatt ttgcgacaga ccaacaacta taacagcgat    420

gatttccagt ttgtgtggaa tatttacgcc aataatgatg tggtggtgcc cactggcggc    480

tgcgatgttt ctgctcgtga tgtcaccgtt actctgccgg actaccctgg ttcagtgccg    540

attcctctta ccgtttattg tgcgaaaagc caaaacctgg ggtattacct ctccggcaca    600

accgcagatg cgggcaactc gattttcacc aataccgcgt cgttttcacc cgcgcagggc    660

gtcggcgtac agttgacgcg caacggtacg attattccag cgaataacac ggtatcgtta    720

ggagcagtag ggacttcggc ggtaagtctg ggattaacgg caaattacgc acgtaccgga    780

gggcaggtga ctgcagggaa tgtgcaatcg attattggcg tgacttttgt ttatcaa       837


<210> SEQ ID NO 23
<211> LENGTH: 279
<212> TYPE: PRT
<213> ORGANISM: E. coli

<400> SEQUENCE: 23

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Ile Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Ala Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Ala Arg Asn Gly Thr Val Ile Pro Ala Asn Asn Thr Val Ser Leu
225                 230                 235                 240
```

-continued

```
Gly Ala Val Gly Thr Ser Ala Val Ser Leu Gly Leu Thr Ala Asn Tyr
            245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 24
<211> LENGTH: 279
<212> TYPE: PRT
<213> ORGANISM: E. coli

<400> SEQUENCE: 24

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Ile Val Lys Tyr Asn Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Ala Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 25
<211> LENGTH: 279
<212> TYPE: PRT
<213> ORGANISM: E. coli

<400> SEQUENCE: 25
```

-continued

```
Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ala Ala Tyr
    50                  55                  60

Gly Gly Val Leu Ser Ser Phe Ser Gly Thr Val Lys Tyr Asn Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 26
<211> LENGTH: 279
<212> TYPE: PRT
<213> ORGANISM: E. coli

<400> SEQUENCE: 26

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ala Ala Tyr
    50                  55                  60

Gly Gly Val Leu Ser Ser Phe Ser Gly Thr Val Lys Tyr Asn Gly Ser
65                  70                  75                  80

Ser Tyr Pro Phe Pro Thr Thr Ser Glu Thr Pro Arg Val Val Tyr Asn
                85                  90                  95
```

-continued

```
Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 27
<211> LENGTH: 279
<212> TYPE: PRT
<213> ORGANISM: E. coli

<400> SEQUENCE: 27

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala His Asp Val Thr Val Thr Leu Pro Asp Tyr Arg
                165                 170                 175

Gly Ser Val Pro Ile Pro Leu Thr Val Tyr Cys Ala Lys Ser Gln Asn
```

```
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 28
<211> LENGTH: 279
<212> TYPE: PRT
<213> ORGANISM: E. coli

<400> SEQUENCE: 28

Phe Ala Cys Lys Thr Ala Asn Gly Thr Ala Ile Pro Ile Gly Gly Gly
1               5                   10                  15

Ser Ala Asn Val Tyr Val Asn Leu Ala Ile Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Val Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270
```

```
Gly Ala Thr Phe Val Tyr Gln
        275


<210> SEQ ID NO 29
<211> LENGTH: 279
<212> TYPE: PRT
<213> ORGANISM: E. coli

<400> SEQUENCE: 29

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Leu Val Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Thr Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 30
<211> LENGTH: 280
<212> TYPE: PRT
<213> ORGANISM: E. coli

<400> SEQUENCE: 30

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30
```

-continued

```
Asn Leu Val Val Asp Leu Ser Thr Gln Thr Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala His Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln Glx
        275                 280


<210> SEQ ID NO 31
<211> LENGTH: 279
<212> TYPE: PRT
<213> ORGANISM: E. coli

<400> SEQUENCE: 31

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Asn Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125
```

-continued

```
Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Ala Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 32
<211> LENGTH: 279
<212> TYPE: PRT
<213> ORGANISM: E. coli

<400> SEQUENCE: 32

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Val Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
        195                 200                 205

Phe Thr Asn Thr Ala Ser Phe Ser Pro Ala Gln Gly Val Gly Val Gln
```

-continued

```
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 33
<211> LENGTH: 279
<212> TYPE: PRT
<213> ORGANISM: E. coli

<400> SEQUENCE: 33

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ala Ala Tyr
    50                  55                  60

Gly Gly Val Leu Ser Ser Phe Ser Gly Thr Val Lys Tyr Asn Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 34
<211> LENGTH: 279
```

<212> TYPE: PRT
<213> ORGANISM: E. coli

<400> SEQUENCE: 34

```
Phe Ala Cys Lys Thr Ala Asn Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275
```

<210> SEQ ID NO 35
<211> LENGTH: 279
<212> TYPE: PRT
<213> ORGANISM: E. coli

<400> SEQUENCE: 35

```
Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60
```

-continued

```
Gly Ser Val Leu Ser Ser Phe Ser Gly Thr Val Lys Tyr Asn Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 36
<211> LENGTH: 279
<212> TYPE: PRT
<213> ORGANISM: E. coli

<400> SEQUENCE: 36

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Val Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160
```

```
Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Arg Ser Ile Ile
            260                 265                 270

Ala Val Thr Phe Val Tyr Gln
        275


<210> SEQ ID NO 37
<211> LENGTH: 279
<212> TYPE: PRT
<213> ORGANISM: E. coli

<400> SEQUENCE: 37

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Glu Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
```

```
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 38
<211> LENGTH: 279
<212> TYPE: PRT
<213> ORGANISM: E. coli

<400> SEQUENCE: 38

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser His Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Met Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Asn Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 39
<211> LENGTH: 279
<212> TYPE: PRT
<213> ORGANISM: E. coli

<400> SEQUENCE: 39

Phe Ala Cys Lys Thr Ala Asn Gly Thr Ala Ile Pro Ile Gly Gly Gly
```

-continued

```
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Val Arg Asp Val Thr Val Ile Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Lys Ser Ile Ile
            260                 265                 270

Gly Val Thr Phe Val Tyr Gln
        275


<210> SEQ ID NO 40
<211> LENGTH: 279
<212> TYPE: PRT
<213> ORGANISM: E. coli

<400> SEQUENCE: 40

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Asn Gly Ser
65                  70                  75                  80

Ser Tyr Pro Phe Pro Thr Thr Ser Glu Thr Pro Arg Val Val Tyr Asn
                85                  90                  95
```

-continued

```
Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Ala Asn Gly Thr Ile Val Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 41
<211> LENGTH: 279
<212> TYPE: PRT
<213> ORGANISM: E. coli

<400> SEQUENCE: 41

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Ser Phe Ser Gly Thr Val Lys Tyr Asn Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Leu Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190
```

```
Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 42
<211> LENGTH: 279
<212> TYPE: PRT
<213> ORGANISM: E. coli

<400> SEQUENCE: 42

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Asn Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
```

275

<210> SEQ ID NO 43
<211> LENGTH: 279
<212> TYPE: PRT
<213> ORGANISM: E. coli

<400> SEQUENCE: 43

```
Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Lys Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Thr Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275
```

<210> SEQ ID NO 44
<211> LENGTH: 279
<212> TYPE: PRT
<213> ORGANISM: E. coli

<400> SEQUENCE: 44

```
Phe Ala Cys Lys Thr Ala Asn Gly Thr Ala Ile Pro Ile Gly Gly Gly
1               5                   10                  15

Ser Ala Asn Val Tyr Val Asn Leu Ala Pro Val Val Asn Val Gly Gln
            20                  25                  30

Asn Leu Val Val Asp Leu Ser Thr Gln Ile Phe Cys His Asn Asp Tyr
```

-continued

```
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Pro
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr Thr Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 45
<211> LENGTH: 279
<212> TYPE: PRT
<213> ORGANISM: E. coli

<400> SEQUENCE: 45

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ala Ala Tyr
    50                  55                  60

Gly Gly Val Leu Ser Ser Phe Ser Gly Thr Val Lys Tyr Asn Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125
```

-continued

```
Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270

Gly Val Thr Phe Val Tyr Gln
        275


<210> SEQ ID NO 46
<211> LENGTH: 7416
<212> TYPE: DNA
<213> ORGANISM: Artificial Sequence
<220> FEATURE:
<223> OTHER INFORMATION: Sequence of Plasmid pCGA126-1

<400> SEQUENCE: 46

gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgag taataaaaac gtcaatgtaa    240

ggaaatcgca ggaaataaca ttctgcttgc tggcaggtat cctgatgttc atggcaatga    300

tggttgccgg acgcgctgaa gcgggagtgg ccttaggtgc gactcgcgta atttatccgg    360

cagggcaaaa acaagtgcaa cttgccgtga caaataatga tgaaaatagt acctatttaa    420

ttcaatcatg ggtggaaaat gccgatggtg taaaggatgg tcgttttatc gtgacgcctc    480

ctctgtttgc gatgaaggga aaaaaagaga ataccttacg tattcttgat gcaacaaata    540

accaattgcc acaggaccgg gaaagtttat tctggatgaa cgttaaagcg attccgtcaa    600

tggataaatc aaaattgact gagaatacgc tacagctcgc aattatcagc cgcattaaac    660

tgtactatcg cccggctaaa ttagcgttgc cacccgatca ggccgcagaa aaattaagat    720

ttcgtcgtag cgcgaattct ctgacgctga ttaacccgac accctattac ctgacggtaa    780

cagagttgaa tgccggaacc cgggttcttg aaaatgcatt ggtgcctcca atgggcgaaa    840

gcacggttaa attgccttct gatgcaggaa gcaatattac ttaccgaaca ataaatgatt    900

atggcgcact tacccccaaa atgacgggcg taatggaata atagatctca cgacaggttt    960

cccgactgga aagcgggcag tgagcgcaac gcaattaatg tgagttagct cactcattag   1020

gcaccccagg ctttacactt tatgcttccg gctcgtatgt tgtgtggaat tgtgagcgga   1080

taacaatttc acacaggaaa cagctatgaa acgagttatt accctgtttg ctgtactgct   1140

gatgggctgg tcggtaaatg cctggtcatt cgcctgtaaa accgccaatg gtaccgctat   1200
```

-continued

```
ccctattggc ggtggcagcg ccaatgttta tgtaaacctt gcgcccgtcg tgaatgtggg   1260
gcaaaacctg gtcgtggatc tttcgacgca aatcttttgc cataacgatt atccggaaac   1320
cattacagac tatgtcacac tgcaacgagg ctcggcttat ggcggcgtgt tatctaattt   1380
ttccgggacc gtaaaatata gtggcagtag ctatccattt cctaccacca gcgaaacgcc   1440
gcgcgttgtt tataattcga gaacggataa gccgtggccg gtggcgcttt atttgacgcc   1500
tgtgagcagt gcgggcgggg tggcgattaa agctggctca ttaattgccg tgcttatttt   1560
gcgacagacc aacaactata acagcgatga tttccagttt gtgtggaata tttacgccaa   1620
taatgatgtg gtggtgccta ctggcggctg cgatgtttct gctcgtgatg tcaccgttac   1680
tctgccggac taccctggtt cagtgccaat tcctcttacc gtttattgtg cgaaaagcca   1740
aaacctgggg tattacctct ccggcacaac cgcagatgcg ggcaactcga ttttcaccaa   1800
taccgcgtcg ttttcacctg cacagggcgt cggcgtacag ttgacgcgca acggtacgat   1860
tattccagcg aataacacgg tatcgttagg agcagtaggg acttcggcgg tgagtctggg   1920
attaacggca aattatgcac gtaccggagg gcaggtgact gcagggaatg tgcaatcgat   1980
tattggcgtg acttttgttt atcaataagg atccgtcgac ctgcaggcat gcaagcttgg   2040
cactggccgt cgttttacaa cgtcgtgact gggaaaaccc tggcgttacc caacttaatc   2100
gccttgcagc acatccccct ttcgccagct ggcgtaatag cgaagaggcc cgcaccgatc   2160
gcccttccca acagttgcgc agcctgaatg gcgaatggcg cctgatgcgg tattttctcc   2220
ttacgcatct gtgcggtatt tcacaccgca taaattccct gttttggcgg atgagagaag   2280
attttcagcc tgatacagat taaatcagaa cgcagaagcg gtctgataaa acagaatttg   2340
cctggcggca gtagcgcggt ggtcccacct gaccccatgc cgaactcaag aagtgaaacg   2400
ccgtagcgcc gatggtagtg ttggggtctc cccatgcgag agtagggaac tgccaggcat   2460
caaataaaac gaaaggctca gtcgaaagac tgggcctttc gttttatctg ttgtttgtcg   2520
gtgaacgctc tcctgagtag gacaaatccg ccgggagcgg atttgaacgt tgcgaagcaa   2580
cggcccgggg tgggcgggca ggacgcccgc catatactgc caggcatcaa attaagcata   2640
aggccatctg acgtatggcc tttttgcgtt tttacaacct cttccgtcca cctgacccca   2700
tgccgaactc aaagtgaaac gccgtagcgc cgatggtagt gtggggtctc cccatgcgag   2760
agtagggaac tgccaggcat caaataaaac gaaaggctca gtcgaaagac tgggcctttc   2820
gttttatctg ttgtttgtcg gtgaacgctc tcctgagtag gacaaatccg cccgggagcg   2880
gatttgaacg ttgcgaagca acggcccgga gggtggcggg caggacgccc gccataaact   2940
gccaggcatc aaattaagca gaaggccatc ctgacggatg gcctttttgc gtttctacaa   3000
actcttcctg tcgtcatatc tacaagccat ccccccacag atacggtaaa ctagcctcgt   3060
ttttgcatca ggaaagcagg gaatttatgg tgcactctca gtacaatctg ctctgatgcc   3120
gcatagttaa gccagccccg acacccgcca acacccgctg acgcgccctg acgggcttgt   3180
ctgctcccgg catccgctta cagacaagct gtgaccgtct ccgggagctg catgtgtcag   3240
aggttttcac cgtcatcacc gaaacgcgcg agacgaaagg gccatgaaca ataaaactgt   3300
ctgcttacat aaacagtaat acaaggggtg ttatgagcca tattcaacgg gaaacgtctt   3360
ctctaggccg cgattaaatt ccaacatgga tgctgattta tatgggtata aatgggctcg   3420
cgataatgtc gggcaatcag gtgcgacaat ctatcgattg tatgggaagc ccgatgcgcc   3480
agagttgttt ctgaaacatg gcacaggtag cgctgccaat gatgttacag atgagatggt   3540
```

-continued

```
cagactaaac tggctgacgg aatttatgcc tcttcgacca tcaaccattt tatccgtact   3600
cctgatgatg catggttact caccactgcg atccccggaa aacagcattc caggtattag   3660
aagaatatcc tgattcaggt gaaaatattg ttgatgcgct ggcagtgttc ctgcgccggt   3720
tgcattcgat tcctgtttgt aattgtcctt ttaacagcga tcgcgtattt cgtctcgctc   3780
aggcgcaatc accaatgaat aacggtttgg ttgatgcgag tgattttgat gacgagcgta   3840
atggctggcc tgttgaacaa gtctggaaag aaatgcataa acttttgcca ttctcaccgg   3900
attcagtcgt cactcatggt gatttctcac ttaataacct tatttttgac gaggggaaat   3960
taataggttg tattgatgtt ggacgagtcg gaatcgcaga ccgataccag gatcttgcca   4020
tcctatggaa ctgcctcggt gagttttctc cttcattaca gaaacggctt tttcaaaaat   4080
atggtattga taatcctgat atgaataaat tgcagtttca tttgatgctc gatgagtttt   4140
tctaagaatt aattcatggc cctcgtgata cgcctatttt tataggttaa tgtcatgata   4200
ataatggttt cttagacgtg aggttctgta cccgacacca tcgaatggcg caaaaccttt   4260
cgcggtatgg catgatagcg cccggaagag agtcaattca gggtggtgaa tgtgaaacca   4320
gtaacgttat acgatgtcgc agagtatgcc ggtgtctctt atcagaccgt ttcccgcgtg   4380
gtgaaccagg ccagccacgt ttctgcgaaa acgcgggaaa aagtggaagc ggcgatggcg   4440
gagctgaatt acattcccaa ccgcgtggca caacaactgg cgggcaaaca gtcgttgctg   4500
attggcgttg ccacctccag tctggccctg cacgcgccgt cgcaaattgt cgcggcgatt   4560
aaatctcgcg ccgatcaact gggtgccagc gtggtggtgt cgatggtaga acgaagcggc   4620
gtcgaagcct gtaaagcggc ggtgcacaat cttctcgcgc aacgcgtcag tgggctgatc   4680
attaactatc cgctggatga ccaggatgcc attgctgtgg aagctgcctg cactaatgtt   4740
ccggcgttat ttcttgatgt ctctgaccag acacccatca acagtattat tttctcccat   4800
gaagacggta cgcgactggg cgtggagcat ctggtcgcat tgggtcacca gcaaatcgcg   4860
ctgttagcgg gcccattaag ttctgtctcg gcgcgtctgc gtctggctgg ctggcataaa   4920
tatctcactc gcaatcaaat tcagccgata gcggaacggg aaggcgactg gagtgccatg   4980
tccggttttc aacaaaccat gcaaatgctg aatgagggca tcgttcccac tgcgatgctg   5040
gttgccaacg atcagatggc gctgggcgca atgcgcgcca ttaccgagtc cgggctgcgc   5100
gttggtgcgg atatctcggt agtgggatac gacgataccg aagacagctc atgttatatc   5160
ccgccgttaa ccaccatcaa acaggatttt cgcctgctgg ggcaaaccag cgtggaccgc   5220
ttgctgcaac tctctcaggg ccaggcggtg aagggcaatc agctgttgcc cgtctcactg   5280
gtgaaaagaa aaaccaccct ggcgcccaat acgcaaaccg cctctccccg cgcgttggcc   5340
gattcattaa tgcagctggc acgacaggtt tcccgactgg aaagcgggca gtgagcgcaa   5400
cgcaattaat ggtaagttag ctcactcatt aggcacccca ggctttaca ctttatgctt   5460
ccgacctgga agaacctgac gtcaggtggc acttttcggg gaaatgtgcg cggaacccct   5520
atttgtttat ttttctaaat acattcaaat atgtatccgc tcatgagaca ataaccctga   5580
taaatgcttc aataatattg aaaaaggaag agtatgagta ttcaacattt ccgtgtcgcc   5640
cttattccct tttttgcggc attttgcctt cctgtttttg ctcacccaga aacgctggtg   5700
aaagtaaaag atgctgaaga tcagttgggt gcacgagtgg gttacatcga actggatctc   5760
aacagcggta agatccttga gagttttcgc cccgaagaac gttttccaat gatgagcact   5820
tttaaagttc tgctatgtgg cgcggtatta tcccgtattg acgccgggca agagcaactc   5880
gggtcgccgc atacactatt ctcagaatga cttggttgag tactcaccag tcacagaaaa   5940
```

```
gcatcttacg gatggcatga cagtaagaga attatgcagt gctgccataa ccatgagtga   6000

taacactgcg gccaacttac ttctgacaac gatcggagga ccgaaggagc taaccgcttt   6060

tttgcacaac atgggggatc atgtaactcg ccttgatcgt tgggaaccgg agctgaatga   6120

agccatacca aacgacgagc gtgacaccac gatgcctgta gcaatgcaac aacgttggcg   6180

caaactatta actggcgaac tacttactct agcttcccgg caacaattaa tagactggat   6240

ggaggcggat aaagttgcag gaccacttct gcgctcggcc cttccggctg gctggtttat   6300

tgctgataaa tctggagccg gtgagcgtgg gtctcgcggt atcattgcag cactggggcc   6360

agatggtaag ccctcccgta tcgtagttat ctacacgacg gggagtcagg caactatgga   6420

tgaacgaaat agacagatcg ctgagatagg tgcctcactg attaagcatt ggtaactgtc   6480

agaccaagtt tactcatata tactttagat tgatttaaaa cttcattttt aatttaaaag   6540

gatctaggtg aagatccttt ttgataatct catgaccaaa atcccttaac gtgagttttc   6600

gttccactga gcgtcagacc ccgtagaaaa gatcaaagga tcttcttgag atcctttttt   6660

tctgcgcgta atctgctgct tgcaaacaaa aaaaccaccg ctaccagcgg tggtttgttt   6720

gccggatcaa gagctaccaa ctctttttcc gaaggtaact ggcttcagca gagcgcagat   6780

accaaatact gttcttctag tgtagccgta gctaggccac cacttcaaga actctgtagc   6840

accgcctaca tacctcgctc tgctaatcct gttaccagtg gctgctgcca gtggcgataa   6900

gtcgtgtctt accgggttgg actcaagacg atagttaccg gataaggcgc agcggtcggg   6960

ctgaacgggg ggttcgtgca cacagcccag cttggagcga acgacctaca ccgaactgag   7020

atacctacag cgtgagctat gagaaagcgc cacgcttccc gaagggagaa aggcggacag   7080

gtatccggta agcggcaggg tcggaacagg agagcgcacg agggagcttc caggggggaaa  7140

cgcctggtat ctttatagtc ctgtcgggtt tcgccacctc tgacttgagc gtcgattttt   7200

gtgatgctcg tcaggggggc ggagcctatg gaaaaacgcc agcaacgcgg cctttttacg   7260

gttcctggcc ttttgctggc cttttgctca catgttcttt cctgcgttat cccctgattc   7320

tgtggataac cgtattaccg cctttgagtg agctgatacc gctcgccgca gccgaacgac   7380

cgagcgcagc gagtcagtga gcgaggaagc ggaaga                             7416
```

```
<210> SEQ ID NO 47
<211> LENGTH: 726
<212> TYPE: DNA
<213> ORGANISM: Artificial Sequence
<220> FEATURE:
<223> OTHER INFORMATION: Sequence of J96 fimC plus native signal sequence

<400> SEQUENCE: 47

atgagtaata aaaacgtcaa tgtaaggaaa tcgcaggaaa taacattctg cttgctggca     60

ggtatcctga tgttcatggc aatgatggtt gccggacgcg ctgaagcggg agtggcctta    120

ggtgcgactc gcgtaattta tccggcaggg caaaaacaag tgcaacttgc cgtgacaaat    180

aatgatgaaa atagtaccta tttaattcaa tcatgggtgg aaaatgccga tggtgtaaag    240

gatggtcgtt ttatcgtgac gcctcctctg tttgcgatga agggaaaaaa agagaatacc    300

ttacgtattc ttgatgcaac aaataaccaa ttgccacagg accgggaaag tttattctgg    360

atgaacgtta aagcgattcc gtcaatggat aaatcaaaat tgactgagaa tacgctacag    420

ctcgcaatta tcagccgcat taaactgtac tatcgcccgg ctaaattagc gttgccaccc    480

gatcaggccg cagaaaaatt aagatttcgt cgtagcgcga attctctgac gctgattaac    540
```

ccgacaccct attacctgac ggtaacagag ttgaatgccg gaacccgggt tcttgaaaat 600
gcattggtgc ctccaatggg cgaaagcacg gttaaattgc cttctgatgc aggaagcaat 660
attacttacc gaacaataaa tgattatggc gcacttaccc ccaaaatgac gggcgtaatg 720
gaataa 726

<210> SEQ ID NO 48
<211> LENGTH: 903
<212> TYPE: DNA
<213> ORGANISM: Artificial Sequence
<220> FEATURE:
<223> OTHER INFORMATION: Sequence J96 fimH plus native signal sequence

<400> SEQUENCE: 48
atgaaacgag ttattaccct gtttgctgta ctgctgatgg gctggtcggt aaatgcctgg 60
tcattcgcct gtaaaaccgc caatggtacc gctatcccta ttggcggtgg cagcgccaat 120
gtttatgtaa accttgcgcc cgtcgtgaat gtggggcaaa acctggtcgt ggatctttcg 180
acgcaaatct tttgccataa cgattatccg gaaaccatta cagactatgt cacactgcaa 240
cgaggctcgg cttatggcgg cgtgttatct aatttttccg ggaccgtaaa atatagtggc 300
agtagctatc catttcctac caccagcgaa acgccgcgcg ttgtttataa ttcgagaacg 360
gataagccgt ggccggtggc gctttatttg acgcctgtga gcagtgcggg cggggtggcg 420
attaaagctg gctcattaat tgccgtgctt attttgcgac agaccaacaa ctataacagc 480
gatgatttcc agtttgtgtg gaatatttac gccaataatg atgtggtggt gcctactggc 540
ggctgcgatg tttctgctcg tgatgtcacc gttactctgc cggactaccc tggttcagtg 600
ccaattcctc ttaccgttta ttgtgcgaaa agccaaaacc tggggtatta cctctccggc 660
acaaccgcag atgcgggcaa ctcgattttc accaataccg cgtcgttttc acctgcacag 720
ggcgtcggcg tacagttgac gcgcaacggt acgattattc cagcgaataa cacggtatcg 780
ttaggagcag tagggacttc ggcggtgagt ctgggattaa cggcaaatta tgcacgtacc 840
ggagggcagg tgactgcagg gaatgtgcaa tcgattattg gcgtgacttt tgtttatcaa 900
taa 903

<210> SEQ ID NO 49
<211> LENGTH: 814
<212> TYPE: DNA
<213> ORGANISM: Artificial Sequence
<220> FEATURE:
<223> OTHER INFORMATION: Sequence of kanamycin R gene

<400> SEQUENCE: 49
atgagccata ttcaacggga aacgtcttgc tctaggccgc gattaaattc caacatggat 60
gctgatttat atgggtataa atgggctcgc gataatgtcg ggcaatcagg tgcgacaatc 120
tatcgattgt atgggaagcc cgatgcgcca gagttgtttc tgaaacatgg cacaggtagc 180
gctgccaatg atgttacaga tgagatggtc agactaaact ggctgacgga atttatgcct 240
cttcgaccat caaccatttt atccgtactc ctgatgatgc atggttactc accactgcga 300
tccccggaaa acagcattcc aggtattaga agaatatcct gattcaggtg aaaatattgt 360
tgatgcgctg gcagtgttcc tgcgccggtt gcattcgatt cctgtttgta attgtccttt 420
taacagcgat cgcgtatttc gtctcgctca ggcgcaatca ccaatgaata acggtttggt 480
tgatgcgagt gattttgatg acgagcgtaa tggctggcct gttgaacaag tctggaaaga 540
aatgcataaa cttttgccat tctcaccgga ttcagtcgtc actcatggtg atttctcact 600

```
taataacctt atttttgacg aggggaaatt aataggttgt attgatgttg gacgagtcgg    660

aatcgcagac cgataccagg atcttgccat cctatggaac tgcctcggtg agttttctcc    720

ttcattacag aaacggcttt ttcaaaaata tggtattgat aatcctgata tgaataaatt    780

gcagtttcat ttgatgctcg atgagttttt ctaa                                814


<210> SEQ ID NO 50
<211> LENGTH: 1085
<212> TYPE: DNA
<213> ORGANISM: Artificial Sequence
<220> FEATURE:
<223> OTHER INFORMATION: Sequence of Lac IQ

<400> SEQUENCE: 50

atgtgaaacc agtaacgtta tacgatgtcg cagagtatgc cggtgtctct tatcagaccg     60

tttcccgcgt ggtgaaccag gccagccacg tttctgcgaa aacgcgggaa aaagtggaag    120

cggcgatggc ggagctgaat tacattccca accgcgtggc acaacaactg gcgggcaaac    180

agtcgttgct gattggcgtt gccacctcca gtctggccct gcacgcgccg tcgcaaattg    240

tcgcggcgat taaatctcgc gccgatcaac tgggtgccag cgtggtggtg tcgatggtag    300

aacgaagcgg cgtcgaagcc tgtaaagcgg cggtgcacaa tcttctcgcg caacgcgtca    360

gtgggctgat cattaactat ccgctggatg accaggatgc cattgctgtg gaagctgcct    420

gcactaatgt tccggcgtta tttcttgatg tctctgacca gacacccatc aacagtatta    480

ttttctccca tgaagacggt acgcgactgg gcgtggagca tctggtcgca ttgggtcacc    540

agcaaatcgc gctgttagcg ggcccattaa gttctgtctc ggcgcgtctg cgtctggctg    600

gctggcataa atatctcact cgcaatcaaa ttcagccgat agcggaacgg gaaggcgact    660

ggagtgccat gtccggtttt caacaaacca tgcaaatgct gaatgagggc atcgttccca    720

ctgcgatgct ggttgccaac gatcagatgg cgctgggcgc aatgcgcgcc attaccgagt    780

ccgggctgcg cgttggtgcg gatatctcgg tagtgggata cgacgatacc gaagacagct    840

catgttatat cccgccgtta accaccatca aacaggattt tcgcctgctg gggcaaacca    900

gcgtggaccg cttgctgcaa ctctctcagg gccaggcggt gaagggcaat cagctgttgc    960

ccgtctcact ggtgaaaaga aaaaccaccc tggcgcccaa tacgcaaacc gcctctcccc   1020

gcgcgttggc cgattcatta atgcagctgg cacgacaggt ttcccgactg gaaagcgggc   1080

agtga                                                               1085


<210> SEQ ID NO 51
<211> LENGTH: 862
<212> TYPE: DNA
<213> ORGANISM: Sequence of beta-lacyamase gene

<400> SEQUENCE: 51

atgagtattc aacatttccg tgtcgccctt attccctttt ttgcggcatt ttgccttcct     60

gtttttgctc acccagaaac gctggtgaaa gtaaaagatg ctgaagatca gttgggtgca    120

cgagtgggtt acatcgaact ggatctcaac agcggtaaga tccttgagag ttttcgcccc    180

gaagaacgtt ttccaatgat gagcactttt aaagttctgc tatgtggcgc ggtattatcc    240

cgtattgacg ccgggcaaga gcaactcggg tcgccgcata cactattctc agaatgactt    300

ggttgagtac tcaccagtca cagaaaagca tcttacggat ggcatgacag taagagaatt    360

atgcagtgct gccataacca tgagtgataa cactgcggcc aacttacttc tgacaacgat    420
```

-continued

```
cggaggaccg aaggagctaa ccgctttttt gcacaacatg ggggatcatg taactcgcct    480

tgatcgttgg gaaccggagc tgaatgaagc cataccaaac gacgagcgtg acaccacgat    540

gcctgtagca atgcaacaac gttggcgcaa actattaact ggcgaactac ttactctagc    600

ttcccggcaa caattaatag actggatgga ggcggataaa gttgcaggac cacttctgcg    660

ctcggccctt ccggctggct ggtttattgc tgataaatct ggagccggtg agcgtgggtc    720

tcgcggtatc attgcagcac tggggccaga tggtaagccc tcccgtatcg tagttatcta    780

cacgacgggg agtcaggcaa ctatggatga acgaaataga cagatcgctg agataggtgc    840

ctcactgatt aagcattggt aa                                             862


<210> SEQ ID NO 52
<211> LENGTH: 601
<212> TYPE: DNA
<213> ORGANISM: Artificial Sequence
<220> FEATURE:
<223> OTHER INFORMATION: Sequence of the origin of replication

<400> SEQUENCE: 52

tttttctgcg cgtaatctgc tgcttgcaaa caaaaaaacc accgctacca gcggtggttt     60

gtttgccgga tcaagagcta ccaactcttt ttccgaaggt aactggcttc agcagagcgc    120

agataccaaa tactgttctt ctagtgtagc cgtagctagg ccaccacttc aagaactctg    180

tagcaccgcc tacatacctc gctctgctaa tcctgttacc agtggctgct gccagtggcg    240

ataagtcgtg tcttaccggg ttggactcaa gacgatagtt accggataag gcgcagcggt    300

cgggctgaac ggggggttcg tgcacacagc ccagcttgga gcgaacgacc tacaccgaac    360

tgagatacct acagcgtgag ctatgagaaa gcgccacgct tcccgaaggg agaaaggcgg    420

acaggtatcc ggtaagcggc agggtcggaa caggagagcg cacgagggag cttccagggg    480

gaaacgcctg gtatctttat agtcctgtcg ggtttcgcca cctctgactt gagcgtcgat    540

ttttgtgatg ctcgtcaggg gggcggagcc tatggaaaaa cgccagcaac gcggcctttt    600

t                                                                    601


<210> SEQ ID NO 53
<211> LENGTH: 116
<212> TYPE: DNA
<213> ORGANISM: Sequence of Lac p/o

<400> SEQUENCE: 53

cgcaattaat gtgagttagc tcactcatta ggcaccccag gctttacact ttatgcttcc     60

ggctcgtatg ttgtgtggaa ttgtgagcgg ataacaattt cacacaggaa acagct       116


<210> SEQ ID NO 54
<211> LENGTH: 837
<212> TYPE: DNA
<213> ORGANISM: E. coli

<400> SEQUENCE: 54

ttcgcctgta aaaccgccaa tggtaccgct atccctattg gcggtggcag cgccaatgtt     60

tatgtaaacc ttgcgcccgt cgtgaatgtg gggcaaaacc tggtcgtgga tctttcgacg    120

caaatctttt gccataacga ttatccggaa accattacag actatgtcac actgcaacga    180

ggctcggctt atggcggcgt gttatctaat ttttccggga ccgtaaaata taatggcagt    240

agctatccat ttcctaccac cagcgaaacg ccgcgcgttg tttataattc gagaacggat    300

aagccgtggc cggtggcgct ttatttgacg cctgtgagca gtgcgggcgg ggtggcgatt    360
```

```
aaagctggct cattaattgc cgtgcttatt ttgcgacaga ccaacaacta taacagcgat    420

gatttccagt ttgtgtggaa tatttacgcc aataatgatg tggtggtgcc tactggcggc    480

tgcgatgttt ctgctcgtga tgtcaccgtt actctgccgg actaccctgg ttcagtgcca    540

attcctctta ccgtttattg tgcgaaaagc caaaacctgg ggtattacct ctccggcaca    600

accgcagatg cgggcaactc gattttcacc aataccgcgt cgttttcacc tgcacagggc    660

gtcggcgtac agttgacgcg caacggtacg attattccag cgaataacac ggtatcgtta    720

ggagcagtag ggacttcggc ggtgagtctg ggattaacgg caaattatgc acgtaccgga    780

gggcaggtga ctgcagggaa tgtgcaatcg attattggcg tgacttttgt ttatcaa       837
```

```
<210> SEQ ID NO 55
<211> LENGTH: 279
<212> TYPE: PRT
<213> ORGANISM: Artificial Sequence
<220> FEATURE:
<223> OTHER INFORMATION: Consensus sequence of FimH proteins for
                        SEQ ID NO: 23 to 45

<400> SEQUENCE: 55

Phe Ala Cys Lys Thr Ala Asn Gly Thr Ala Ile Pro Ile Gly Gly Gly
1               5                   10                  15

Ser Ala Asn Val Tyr Val Asn Leu Ala Pro Ala Val Asn Val Gly Gln
            20                  25                  30

Asn Leu Val Val Asp Leu Ser Thr Gln Ile Phe Cys His Asn Asp Tyr
        35                  40                  45

Pro Glu Thr Ile Thr Asp Tyr Val Thr Leu Gln Arg Gly Ser Ala Tyr
    50                  55                  60

Gly Gly Val Leu Ser Asn Phe Ser Gly Thr Val Lys Tyr Ser Gly Ser
65                  70                  75                  80

Ser Tyr Pro Phe Pro Thr Thr Ser Glu Thr Pro Arg Val Val Tyr Asn
                85                  90                  95

Ser Arg Thr Asp Lys Pro Trp Pro Val Ala Leu Tyr Leu Thr Pro Val
            100                 105                 110

Ser Ser Ala Gly Gly Val Ala Ile Lys Ala Gly Ser Leu Ile Ala Val
        115                 120                 125

Leu Ile Leu Arg Gln Thr Asn Asn Tyr Asn Ser Asp Asp Phe Gln Phe
    130                 135                 140

Val Trp Asn Ile Tyr Ala Asn Asn Asp Val Val Val Pro Thr Gly Gly
145                 150                 155                 160

Cys Asp Val Ser Ala Arg Asp Val Thr Val Thr Leu Pro Asp Tyr Arg
                165                 170                 175

Gly Ser Val Pro Ile Pro Leu Thr Val Tyr Cys Ala Lys Ser Gln Asn
            180                 185                 190

Leu Gly Tyr Tyr Leu Ser Gly Thr His Ala Asp Ala Gly Asn Ser Ile
        195                 200                 205

Phe Thr Asn Thr Ala Ser Phe Ser Pro Ala Gln Gly Val Gly Val Gln
    210                 215                 220

Leu Thr Arg Asn Gly Thr Ile Ile Pro Ala Asn Asn Thr Val Ser Leu
225                 230                 235                 240

Gly Ala Val Gly Thr Ser Ala Val Ser Leu Gly Leu Thr Ala Asn Tyr
                245                 250                 255

Ala Arg Thr Gly Gly Gln Val Thr Ala Gly Asn Val Gln Ser Ile Ile
            260                 265                 270
```

-continued

```
Gly Val Thr Phe Val Tyr Gln
        275


<210> SEQ ID NO 56
<211> LENGTH: 55
<212> TYPE: DNA
<213> ORGANISM: Artificial Sequence
<220> FEATURE:
<223> OTHER INFORMATION: Oligonucleotide primer GA1F

<400> SEQUENCE: 56

cctgccatgg cgggtgtggc gctgggtgcg acccgcgtga tttatccggc agggc          55


<210> SEQ ID NO 57
<211> LENGTH: 36
<212> TYPE: DNA
<213> ORGANISM: Artificial Sequence
<220> FEATURE:
<223> OTHER INFORMATION: Oligonucleotide primer GA1R

<400> SEQUENCE: 57

ggcgtcgaca gattctatta ttccattacg cccgtc                               36


<210> SEQ ID NO 58
<211> LENGTH: 36
<212> TYPE: DNA
<213> ORGANISM: Artificial Sequence
<220> FEATURE:
<223> OTHER INFORMATION: Oligonucleotide primer GA13F

<400> SEQUENCE: 58

cacacaggaa acagctatga ttgtaatgaa aacgag                               36


<210> SEQ ID NO 59
<211> LENGTH: 39
<212> TYPE: DNA
<213> ORGANISM: Artificial Sequence
<220> FEATURE:
<223> OTHER INFORMATION: Oligonucleotide primer GA6R

<400> SEQUENCE: 59

ggcgtcgacg gatccttatt gataaacaaa agtcacgcc                            39


<210> SEQ ID NO 60
<211> LENGTH: 30
<212> TYPE: DNA
<213> ORGANISM: Artificial Sequence
<220> FEATURE:
<223> OTHER INFORMATION: Oligonucleotide primer GA11F

<400> SEQUENCE: 60

ccgaataaag atatcacgac aggtttcccg                                      30


<210> SEQ ID NO 61
<211> LENGTH: 19
<212> TYPE: DNA
<213> ORGANISM: Artificial Sequence
<220> FEATURE:
<223> OTHER INFORMATION: Oligonucleotide primer GA9R

<400> SEQUENCE: 61

catagctgtt tcctgtgtg                                                  19


<210> SEQ ID NO 62
<211> LENGTH: 23
<212> TYPE: DNA
```

-continued

```
<213> ORGANISM: Artificial Sequence
<220> FEATURE:
<223> OTHER INFORMATION: Oligonucleotide primer GA24F

<400> SEQUENCE: 62

tgctcacatg ttctttcctg cgt                                              23


<210> SEQ ID NO 63
<211> LENGTH: 34
<212> TYPE: DNA
<213> ORGANISM: Artificial Sequence
<220> FEATURE:
<223> OTHER INFORMATION: Oligonucleotide primer GA23R

<400> SEQUENCE: 63

gacgttttta ttactcatag ctgtttcctg tgtg                                  34


<210> SEQ ID NO 64
<211> LENGTH: 37
<212> TYPE: DNA
<213> ORGANISM: Artificial Sequence
<220> FEATURE:
<223> OTHER INFORMATION: Oligonucleotide primer GA21F

<400> SEQUENCE: 64

atgagtaata aaaacgtcaa tgtaaggaaa tcgcagg                               37
```

FIMH ADHESIN PROTEINS AND METHODS OF USE

This application claims the benefit of U.S. provisional application No. 60/216,750, filed Jul. 7, 2000, the disclosure of which is hereby incorporated by reference in its entirety.

FIELD OF THE INVENTION

This invention relates to bacterial adhesin proteins and active fragments thereof for use in vaccine compositions for the prevention, diagnosis and treatment of bacterial induced diseases such as those of the urinary tract, especially to the use of such adhesins as immunogenic agents in humans and animals to stimulate an immune response.

BACKGROUND OF THE INVENTION

Urinary tract infections (herein, "UTI") present a disease process that is mediated by the attachment of bacteria to cells. *Escherichia coli* is the most common pathogen of the urinary tract, accounting for more than 85% of cases of asymptomatic bacteriuria, acute cystitis and acute pyelonephritis, as well as greater than 60% of recurrent cystitis, and at least 35% of recurrent pyelonephritis infections. Furthermore, approximately 25%–30% of women experience a recurrent *E. coli* urinary tract infection within the first 12 months following an initial infection but after a second or third infection the rate of recurrence increases to 60%–75%. Given the high incidence, continued persistence, and significant expense associated with *E. coli* urinary tract infections, there is a need for a prophylactic vaccine to reduce susceptibility to this disease.

While many factors contribute to the acquisition and progression of *E. coli* urinary tract infections, it is generally accepted that colonization of the urinary epithelium is a required step in the infection process. In a typical course of *E. coli* urinary tract infection, bacteria originate from the bowel, ascend into the bladder, and adhere to the bladder mucosa where they multiply and establish an infection (cystitis) before ascending into the ureters and kidneys. Disruption or prevention of pilus-mediated attachment of *E. coli* to urinary epithelia may prevent or retard the development of urinary tract infections. In this regard, a number of studies have pointed to a role for pili in mediating attachment to host uroepithelial cells.

To initiate infection bacterial pathogens must first be able to colonize an appropriate target tissue of the host. For many pathogens this tissue is located at a mucosal surface. Colonization begins with the attachment of the bacterium to receptors expressed by cells forming the lining of the mucosa. Attachment is mediated via proteins on the bacterium that bind specifically to cellular receptors. These proteins, or adhesins, are expressed either directly on the surface of the bacterium, or more typically, as components of elongated rod-like protein structures called pili, fimbriae or fibrillae.

Type 1 pili are thought to be important in initiating colonization of the bladder and inducing cystitis, whereas P pili are thought to play a role in ascending infections and the ensuing pyelonephritis.

Such pili are heteropolymeric structures that are composed of several different structural proteins required for pilus assembly. Two types of pili are of particular interest: P pili and type 1 pili. P pili-carrying bacteria recognize and bind to the gal-(α1-4)gal moiety present in the globoseries of glycolipids on kidney cells in mammals. Type 1 pili-carrying bacteria recognize and bind to D-mannose in glycolipids and glycoproteins of bladder epithelial cells.

FimH is the D-mannose-binding adhesin that promotes attachment of type 1 piliated bacteria to host cells via mannose-containing glycoproteins on eukaryotic cell surfaces. FimC is its periplasmic chaperone protein.

In this specification, the terms "pili", "fimbriae," and "fibrillae" are used to refer to heteropolymeric protein structures located on the extracellular surface of bacteria, most commonly gram-negative bacteria. Typically these structures are anchored in the outer membrane. Throughout this specification the terms pilus, pili, fimbriae, and fibrilla will be used interchangeably.

As used herein, the term "periplasmic chaperone" is defined as a protein localized in the periplasm of bacteria that is capable of forming complexes with a variety of chaperone-binding proteins via recognition of a common binding epitope (or epitopes). Chaperones serve as templates upon which proteins exported from the bacterial cell into the periplasm fold into their native conformations. Association of the chaperone-binding protein with the chaperone also serves to protect the binding proteins from degradation by proteases localized within the periplasm, increases their solubility in aqueous solution, and leads to their sequentially correct incorporation into an assembling pilus.

Chaperone proteins are a class of proteins in gram-negative bacteria that are involved in the assembly of pili by mediating such assembly, but are not incorporated into the structure. FimC is the periplasmic chaperone protein that mediates assembly of type 1 pili in bacteria.

It has recently been reported that such chaperones can direct formation of the appropriate native structure of the corresponding adhesin or pilin by inserting a specific fold of the chaperone protein in place of a missing domain or helical strand of the chaperone or pilin. Thus, FimH proteins tend to have their native structure in the presence of such a chaperone but not in its absence. [see: Choudhury et al, X-ray Structure of the FimC-FimH Chaperone-Adhesin Complex from Uropathogenic *E. coli, Science* 285, 1061 (1999); Sauer et al, Structural Basis of Chaperone Function and Pilus Biogenesis, *Science* 285, 1058 (1999)] In addition, recent publications have indicated that the required chaperone strand can be inserted into the adhesin or pilin protein, such as FimH, to provide the missing structure and produce the correct native structure; Barnhart, M. M. et al., PapD-like Chaperones Provide the Missing Information for Folding of Pilin Proteins, *Proc. Natl. Acad. Sci.* (*USA*), 10.1073/pnas.130183897 (published online Jun. 20, 2000).

Antibodies directed against purified whole type 1 or P pili protect against cystitis and pyelonephritis, respectively, in both murine and primate models for these diseases. See: Abraham et al., *Infect Immun.* 48:625 (1985), Roberts et al., *Proc. Natl. Acad. Sci. (USA)* 91:11889 (1994), O'Hantey et al., *J. Clin. Invest.* 75: 347 (1985). However, such protection is limited to either homologous *E. coli* strains from which the pili used as immunogens were derived, or to a small subset of serologically cross-reactive heterologous strains. Therefore, vaccines composed predominantly of the major structural proteins of pili (i.e., PapA or FimA) appear to be of limited value because antibodies developed against these highly variable proteins are specific for the strains used for immunization.

Furthermore, antibodies to FimH have been found to be protective. Barnhart, M. M. et al., PapD-like Chaperones Provide the Missing Information for Folding of Pilin Proteins, *Proc. Natl. Acad. Sci.* (*USA*), 10.1073/pnas.130183897 (published online Jun. 20, 2000).

Recently, Sokurenko et al [see: *J. Bacteriol.* 177, 3680–86 (1995)] have found that quantitative variations in mannosesensitive adhesion of *E. coli* are due primarily to structural differences in the FimH adhesin. Further research has shown that the ability of the FimH lectins to interact with mono-mannosyl residues strongly correlates with their ability to mediate *E. coli* adhesion to uroepithelial cells so that certain phenotypic variants of type 1 fimbriae may contribute more than others to the virulence of *E. coli* in the urinary tract. [Sokurenko et al, *J. Biol. Chem.* 272, 17880–17886 (1997)]. Heretofore, random point mutations in FimH genes that increase binding of the adhesin to mono-mannose residues (structures abundant in the oligosaccharide moieties of urothelial glycoproteins) have been found to confer increased virulence in the mouse urinary tract. [See: Sokurenko et al, *Proc. Natl. Acad. Sci. USA* 95, 8922–8926 (1998)]

BRIEF SUMMARY OF THE INVENTION

In one aspect, the present invention relates to immunogenic polypeptides derived from different strains of the bacterium *Escherichia coli* (*E. coli*) which differ from each other in one or more amino acid residues and that induce immunological responses that lead to protection of an animal, especially a human patient, following vaccination with said polypeptides.

It is an object of the present invention to provide immunogenic FimH polypeptides useful as components of vaccines for the prevention and treatment of infections caused by *E. coli*, in particular, urinary tract infections. In specific embodiments, the polypeptides of the present invention have the amino acid sequences shown in FIG. 2. Such vaccine compositions comprising the novel polypeptides disclosed herein are useful in vaccination and treatment of urinary tract infections, especially those caused by *E. coli*. In one embodiment, vaccine compositions according to the invention comprise the polypeptides of FIG. 2 (or truncated segments of the sequences of FIG. 2 which truncates have mannose-binding ability and can serve as vaccines), as stabilized structures in the form of complexes with a chaperone, such as FimC, or with a portion of the sequence of FimC which portion serves to stabilize the structure of the FimH adhesin. A particular embodiment employs the consensus sequence of FIG. 2 (SEQ ID NO: 55).

It is another object of the present invention to provide antibodies, including both polyclonal and monoclonal antibodies, with specificity for the novel polypeptides disclosed herein and whose amino acid sequences are shown in FIG. 2.

It is a still further object of the present invention to provide methods of prophylaxis for the prevention of urinary tract infections using the vaccine compositions disclosed herein.

It is a yet still further object of the present invention to provide methods of treatment of diseases of the urinary tract comprising the use of vaccine compositions as disclosed herein and the use of antibodies generated against such vaccine compositions, and the polypeptides contained therein.

It is another object of the present invention to provide a novel method of preparing polypeptides from recombinant cells using a vector comprising the plasmid of FIGS. 3 through 6. In specific embodiments, the polypeptides comprise the amino acid sequences of FIG. 2. In one embodiment, this process and plasmid can be used to prepare polypeptides that comprise a bacterial chaperone, such as FimC, fused to a bacterial adhesin, such as FimH or any of the polypeptides presented in FIG. 2, including any consensus sequence derived therefrom.

BRIEF DESCRIPTION OF THE DRAWINGS

FIG. 1 shows the nucleotide sequence encoding a number of FimH polypeptides disclosed according to the present invention and derived from *E. coli*. FIGS. 1(*a*) through 1(*j*) follow in sequence.

FIG. 2 shows the amino acid sequences, and sequence variations, for a number of FimH proteins of different strains of *E. coli* with the particular strain listed at the left. FIGS. 1(*a*) through 1(*c*) follow in sequence. A consensus sequence is presented at the bottom. The sequence for FimH of J96 is known in the art.

FIG. 5 is a diagram showing the steps in selection of the final clone pCGA139-1-1.

DETAILED DESCRIPTION OF THE INVENTION

Figure 3:
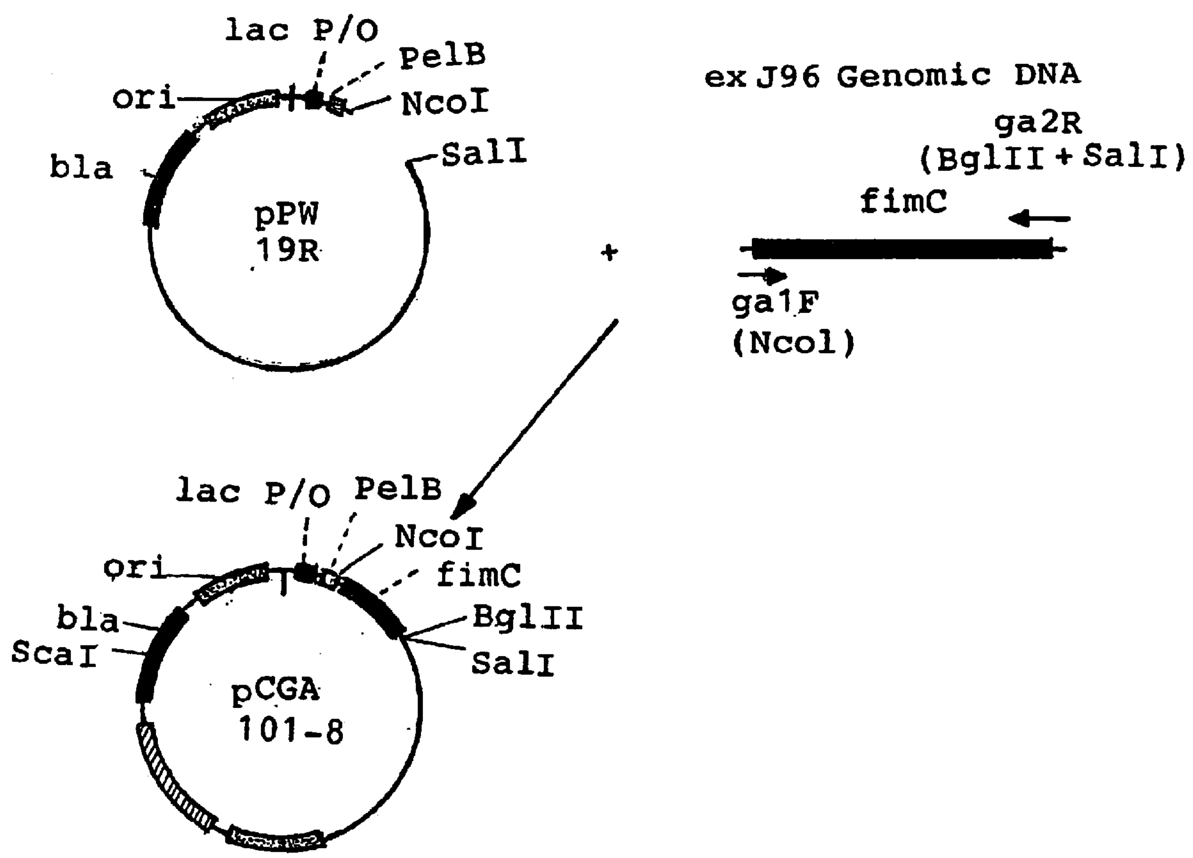
FIG. 3 is a diagram showing the construction of the vector designated as pCGA101-8.

It is an object of the present invention to utilize an immunogenic composition for a vaccine (or to produce antibodies for use as a diagnostic or as a passive vaccine) comprising novel polypeptides, in particular, FimH polypeptides or variants thereof, either alone or in complexed form with a chaperone, or stabilization-inducing portion of a chaperone, or as a series of isolated non-contiguous domains, especially mannose-binding domains, linked together to form a polypeptide, or polypeptide-like, structure.

In one embodiment of the present invention, FimH proteins (naturally or recombinantly produced, as well as functional analogs) from bacteria that produce type 1 pili are contemplated. Even more particularly, *E. coli* FimH proteins are contemplated.

The present invention provides isolated polypeptides comprising a sequence selected from the group consisting of at least residues 26 to 186 of SEQ ID NO: 23 through 45 and 55.

The present invention further relates to isolated polypeptides further comprising about the N-terminal two thirds (which includes about residues 1 through 186) of the sequences selected from SEQ ID NO: 23 through 45 and 55.

The present invention still further relates to isolated polypeptides comprising an amino acid sequence selected from the group consisting of SEQ ID NO: 23 through 45 and 55.

The polypeptides of the present invention may conveniently be present in the form of a composition comprising one or more of the polypeptides in any desired combination or relative concentrations. Further, the present invention includes active truncates, portions, fragments or segments of the novel polypeptides disclosed herein.

The present invention also relates to an isolated polynucleotide encoding one or more of the polypeptides of the present invention, or active truncates, fragments, portions or segments thereof. In one embodiment, the isolated polynucleotides are shown in FIGS. 1(*a*)–1(*j*).

A vaccine composition according to the present invention is one comprising an immunogenically effective amount of a polypeptide of the invention, including immunogenically active truncates, portions, fragments and segments thereof, and in any and all active combinations thereof, wherein said polypeptide, or active fragment, or fragments, is/are suspended in a pharmacologically acceptable carrier, which includes all suitable diluents or excipients.

The present invention also relates to antibodies, either polyclonal or monoclonal, either recombinant or synthetic, specific for any of the polypeptides, as disclosed herein (SEQ ID NO: 23 through 45 and 55) including immunogenically active truncates, portions, fragments and segments of such polypeptides, which antibodies may be used alone or in any and all active combinations thereof.

Such polypeptides, where the entire sequence is used to form a vaccine, are commonly structurally stabilized by complexing with a chaperone, especially FimC (so as to form a FimCH complex—see: Choudhury et al (1999) and Sauer et al (1999), the disclosures of which papers are hereby incorporated by reference in their entirety) or where such structural stabilization is produced by complementing the structure of the adhesin with a portion of a chaperone, such as FimC, that induces the stabilization of the adhesin for use as a vaccine [see Barnhart et al. supra, the disclosure of which is hereby incorporated by reference in its entirety), or where the mannose-binding portions of the sequences of the adhesins of FIG. 2 are isolated from the native molecules, or synthesized, and then joined together to form a structure comprising 1, 2, 3 or more such domains as part of a single polypeptide (other than the native protein) or where such domains are held together by some other chemical linkages.

Because of the immunogenicity and protective properties of the polypeptides and fragments disclosed herein, the present invention further relates to methods for preventing and/or treating disease in an animal, especially a human patient afflicted therewith, comprising administering to said animal an amount of a vaccine composition of the present invention that is effective for such prevention and/or treatment. In specific embodiments of the present invention, said disease is a urinary tract infection or a bladder infection. In preferred embodiments, said disease is caused by a bacterium of the family Enterobacteriaceae, especially *E. coli*, that is effective for such preventing and/or treating.

The present invention further relates to methods of treating disease in an animal, especially a human patient afflicted therewith, comprising administering to said animal a therapeutically effective amount of an antibody of the invention as disclosed hereinabove. In specific embodiments of the present invention, said disease is a urinary tract infection or a bladder infection. In preferred embodiments, said disease is caused by a bacterium of the family Enterobacteriaceae, especially *E. coli.*

The present invention also relates to a recombinant cell expressing a polypeptide, and fragments thereof, selected from the group consisting of SEQ ID NO: 23 through 45, and 55. Here, the term "expressing" means synthesizing a polypeptide from the disclosed polynucleotides of the invention.

The present invention also relates to a vector comprising a polynucleotide selected from the polynucleotides encoding the polypeptides, and active fragments thereof, of the invention.

In accordance with the disclosure herein, the present invention also includes an immunogenic complex comprising a periplasmic chaperone and a polypeptide, or active fragment thereof, selected from the group consisting of the polypeptides of SEQ ID NO: 23 through 45, and 55.

A preferred embodiment of such an immunogenic composition is a composition wherein the active component of said immunogenic composition is a member selected from mannose-binding fragments of FimH adhesin protein variants, or where said proteins are donor complemented single polypeptide structures or present in the form of an immunogenic complex comprising non-contiguous mannose-binding domains derived from said variants (see Langermann, U.S. patent application Ser. No. 60/144,016, filed Jul. 15, 1999, the disclosure of which is hereby incorporated by reference in its entirety).

In another aspect of the invention, immunogenic compositions of the invention may be utilized to produce antibodies to diagnose or treat diseases, especially urinary tract infections, or to produce vaccines for prophylaxis and/or treatment of such infections as well as booster vaccines to maintain a high titer of antibodies against the immunogen(s) of the immunogenic composition.

Applicant has found that FimH polypeptides are highly conserved between various strains of *E. coli*. Moreover, the amino acid changes that occur between strains generally occur at similar amino acid positions.

As a result of the high conservation of FimH between *E. coli* strains, FimH polypeptides from one strain are capable of inducing antibody responses that inhibit or prevent other *E. coli* strains from binding to cells by a FimH lectin and/or provide protection and/or treatment against infection caused by other *E. coli* strains. The SEQ ID NOs. for the FimH proteins (including a consensus sequence) and polynucleotides of the present invention are provided in Table 1 and correlate with the strain designations provided in FIGS. 1 and 2, and the data of Table 2.

There are various ways in which the polypeptides disclosed according to the present invention can be utilized to form therapeutically effective vaccine compositions for use in the prevention and/or treatment of urinary tract and bladder infections, especially those caused by *E. coli.*

In accordance with the teachings herein, the present invention is directed to an immunogenic composition comprising a purified complex of a periplasmic chaperone protein, especially FimC, and a FimH variant according to the invention. The FimC may be obtained from the same *E. coli* strain as the FimH or from a different strain. The FimH polypeptide, or portion thereof, is maintained in the complex in an immunogenic form capable of inducing an immune response when appropriately introduced into a human patient in need thereof. As used herein, the term "patient in need thereof" refers to a human that is infected with, or at risk of being infected with, pathogenic bacteria that produce pili, especially *E. coli* and related bacteria. For research purposes, a mouse model can be utilized to simulate such a patient in some circumstances. See Choudhury, et al., supra, and Sauer, et al., supra.

The polypeptides according to the present invention can also be utilized as components of therapeutically effective vaccine compositions by forming the native structures of said FimH variants without the need for a complex with FimC itself. Thus, the FimH variants as disclosed herein are readily produced by recombinant methods in such a way as to incorporate therein the sequence of FimC required for stabilization (see Barnhart et al (2000)).

An additional means of utilizing the novel polypeptides, or FimH variants, of the present invention is to form synthetic structures comprising non-contiguous domains of said variants. It is known that the cell binding portions of FimH are generally composed of the mannose-binding segments, formed of about the N-terminal two thirds of the molecule. The remaining pilin-binding portion is the segment that interacts with FimC to form a complex in the fibrillum of the bacterial cell. Thus, the FimH variants of the present invention are readily engineered to produce only the specific, and relatively short, mannose-binding domains of the N-terminal two thirds of the sequences depicted in FIG. 2. All or a portion of these domains may be strung together using convenient linker sequences, or other linking structures, to provide polypeptides composed of non-contiguous mannose binding domains, the overall structure of which provides a highly immunogenic structure for use in the vaccine compositions disclosed herein (see Langermann supra).

Of course, these are only three means of utilizing the FimH variants disclosed according to the present invention and other useful embodiments will suggest themselves to those skilled in the relevant arts from the teachings herein.

The proteins, and immunologically active fragments thereof, of the present invention are useful immunogens for preparing vaccine compositions that stimulate the production of antibodies that confer immunity to pathogenic species of bacteria. Further, preparation of vaccines containing purified proteins as antigenic ingredients is well within the level of skill in the art.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system.

Vaccine compositions may, and usually do, incorporate additional substances to stabilize pH, or to function as adjuvants, wetting agents, or emulsifying agents, which can serve to improve the effectiveness of the vaccine.

Vaccines are generally formulated for parenteral administration and are injected either subcutaneously or intramuscularly. Such vaccines can also be formulated as suppositories or for oral administration, using methods known in the art.

The amount of vaccine sufficient to confer immunity to pathogenic bacteria is determined by methods well known to those skilled in the art. This quantity will be determined based upon the characteristics of the vaccine recipient, including considerations of age, sex, and general physical condition, and the level of immunity required. Where vaccines are administered by subcutaneous or intramuscular injection, a range of 1 to 500 $\mu$g purified protein may be given.

In addition to use as vaccines, the FimH variants disclosed herein are available for use as immunogens to stimulate the production of antibodies for use in passive immunotherapy, for use as diagnostic reagents, and for use as reagents in other processes such as affinity chromatography.

In one aspect of the invention complexes comprising the *E. coli* chaperone FimC and a FimH variant of the invention may be formed by co-expressing the appropriate FimH variant polypeptide (of a sequence according to FIG. 2) along with FimC, whose amino acid and nucleotide sequences are known in the art, from a recombinant cell.

In addition, the FimC-FimH complexes useful in vaccines can be recovered from the periplasmic spaces of cells of the indicated strains disclosed herein. These complexes are found in relatively large amounts in recombinant *E. coli* strains which express the FimC protein at levels in excess of those produced in wild type strains. A suitable recombinant strain is C600/pHJ9205, a strain in which expression of FimC has been put under control of the arabinose promoter. Those skilled in the art will recognize that other promoter sequences that can be regulated easily may also be used. Of course, such cells are readily engineered to express one or more of the FimH variant polypeptides of the invention. An extract of periplasm is obtained by exposing the bacteria to lysozyme in the presence of a hypertonic sucrose solution. FimC-H complexes can also be purified using conventional protein purification methods well known in the art.

In a similar manner, FimH fragments that are recombinantly produced either by having *E. coli* produce the full-length FimH variant polypeptides of the present invention and then fragmenting the protein, or the fragment itself, are produced recombinantly may be isolated by mannose-binding affinity purification. Thus, only fragments of the FimH protein that retain mannose binding are isolated. Preferably, such mannose-binding fragments have a label such as a his-tag included and may be purified by methods such as Nickel chromatography.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to a polynucleotides, such terms refer to the products produced by treatment of said polynucleotides with any of the common endonucleases.

The polynucleotides encoding the polypeptides of the invention, for example, those of FIG. 1, may have the coding sequence fused in frame to a marker sequence which allows for purification of the polypeptides of the present invention. The marker sequence may be, for example, a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention also relates to vectors which include polynucleotides encoding one or more of the adhesin proteins of the present invention, host cells which are genetically engineered with vectors of the invention and the production of such adhesin proteins and/or chaperone proteins by recombinant techniques in an isolate and substantially immunogenically pure form.

Host cells are genetically engineered (transduced or transformed or transfected) with the vectors comprising a polynucleotide encoding a chaperone, adhesin protein, mannose binding fragment of an adhesin protein, or the like of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the polynucleotides which encode such polypeptides. The culture conditions, such as temperature, pH and the like, are those previously used with the host cell selected for expression, and will be apparent to the ordinarily skilled artisan.

Vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin or kanamycin resistance in *E. coli.*

For example, optimal expression of a FimH-C complex has been achieved using a newly constructed single vector containing the FimH and FimC genes but having the advantage that each gene is under its own separate lac promoter. Thus, one lac promoter is 5' with respect to FimC while the second lac promoter is 5' to the FimH gene. This plasmid was successfully constructed using the common plasmid pUC19 as a background vector [Yannish-Perron, C., Vierira, J. and Messing, J., *Gene,* 33:103–119 (1985)]. This new plasmid, when used to transform the host *E. coli* strain BL21 [as described in Phillips, T. A., Van Bogelen, R. A., and Neidhart, F. C., *J. Bacteriol.* 159:283–287 (1984)] and then induced using IPTG at the mid-logarithmic stage of growth, gives maximal expression of the FimCH complex in the bacterial periplasmic space. This material is then extracted and purified by methods well known in the art, including those described herein.

The vector containing the appropriate DNA sequence as hereinabove described, as well as an appropriate promoter or control sequence, may be employed to transform an appropriate host to permit the host to express the proteins.

As representative examples of appropriate hosts, there may be mentioned: bacterial cells, such as *E. coli* Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen, Inc.), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacl, lacZ, T3, T7, gpt, lambda PR, PL and TRP. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts, as well as other methods in molecular biology, are described in Sambrook, et al., Molecular Cloning: A Laboratory Manual, Second Edition, Cold Spring Harbor, N.Y., (1989), Wu et al, *Methods in Gene Biotechnology* (CRC Press, New York, N.Y., 1997), and *Recombinant Gene Expression Protocols, in Methods in Molecular Biology*, Vol. 62, (Tuan, ed., Humana Press, Totowa, N.J., 1997), the disclosures of which are hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli Bacillus subtilis, Salmonella typhimurium* and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, a french press, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and/or purified from recombinant cell cultures by well-known protein recovery and purification methods. Such methodology may include ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. In this respect, chaperones may be used in such a refolding procedure. Finally, high performance liquid chromatography (HPLC) can be employed for final purification steps.

The polypeptides that are useful as immunogens in the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated.

Procedures for the isolation of a periplasmic chaperone protein complexed with an adhesin protein are known in the art, as an example see Jones et al., *Proc. Natl. Acad. Sci.* (*USA*) 90:8397–8401 (1993). Further, the individually expressed adhesin proteins may be isolated by recombinant expression/isolation methods that are well-known in the art. Typical examples for such isolation may utilize an antibody to the protein or to a His tag or cleavable leader or tail that is expressing as part of the protein structure.

It is contemplated that the polypeptides of the present invention may be in isolated or purified form.

"Isolated" in the context of the present invention with respect to polypeptides (or polynucleotides) means that the material is removed from its original environment (e.g., the cells used to recombinantly produce the polypeptides disclosed herein). Such peptides could be part of a composition, and still be isolated in that such vector or composition is not part of its natural environment. The polypeptides and polynucleotides of the present invention are preferably provided in an isolated form, and preferably are purified to homogeneity.

The recombinant and/or immunogenic polypeptides, disclosed in accordance with the present invention, may also be in "purified" form. The term "purified" does not require absolute purity; rather, it is intended as a relative definition, and can include preparations that are highly purified or preparations that are only partially purified, as those terms are understood by those of skill in the relevant art. For example, polypeptides from individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, claimed polypeptides having a purity of preferably 0.001%, or at least 0.01% or 0.1%, and even desirably 1% by weight or greater is expressly contemplated.

For purposes of recombinantly producing the polypeptides of the invention, the term "expression product" means that polypeptide or protein that is the natural translation product of the gene and any nucleic acid sequence coding equivalents resulting from genetic code degeneracy and thus coding for the same amino acid(s).

The FimCH polypeptides useful in forming the vaccine compositions of the present invention may conveniently be cloned using various cloning systems. An example of a useful cloning system for synthesizing FimCH molecules that may incorporate any of the FimH sequences disclosed herein (see FIG. 2) is presented in Example 2 and utilizes a plasmid based cloning system. The FimCH complex described therein is composed of a 52 kDa complex composed of two proteins: FimC (22.8 kDa) and FimH (29.1 kDa) in a 1:1 equimolar ratio. The FimCH complex is expressed from a pUC-based vector (pGCA139-1-1) with two separate lac-inducible promoters driving expression of the FimC and FimH genes, respectively. The FimC and the FimH genes in the pGCA139-1-1 vector were derived from uropathogenic *E. coli* isolate J96.

The FimCH complex is produced in the periplasm of *E. coli* strain BL21 and is purified from periplasmic extracts by standard chromatographic methods. The FimCH protein has been formulated in a number of different buffers compatible with its solubility profile including 20 mM HEPES (pH 7.0), PBS (pH 7.0) and sodium citrate (pH 6.0)+0.2 M NaCl. This sodium citrate/sodium chloride formulation enhances the stability of the FimCH complex and is also compatible with commonly used diluents.

Plasmid pCGA139-1-1 was constructed as a means of producing relatively large amounts of *E. coli* chaperone-adhesin complex, FimCH, for use in the vaccine compositions disclosed herein. Such vaccines act by blocking adherence of *E. coli* to the mucosa of the urinary tract thus preventing colonization which often results in infection.

The plasmid vector, pCGA139-1-1, contains the following genetic elements: (1) an *E. coli* FimC chaperone gene followed by (2) the fimH adhesin gene, both from *E. coli* strain J96 (a urinary tract infection (UTI) isolate) each preceeded by its respective native signal sequence (nss); (3) a kanamycin resistance ($kan^r$ or $k^r$) marker; (4) $lacI^q$ which codes for a repressor protein that binds the lac promoter unless it is induced; (5) an inactivated beta-lactamase (bla) gene; (6) pUC origin of replication (ori); and (7) two lac promoters, one preceding the fimC signal and the other preceding that of fimH.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the variant FimH polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides.

For preparation of monoclonal antibodies, any technique which provides antibodies produced by continuous cell line cultures can be used. Examples include the hybridoma technique (Kohler and Milstein, *Nature,* 256:495–497 (1975)), the trioma technique, the human B-cell hybridoma technique (Kozbor et al., *Immunology Today* 4:72 (1983)), and the EBV-hybridoma technique to produce human monoclonal antibodies (Cole, et al. (1985) in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

In order to facilitate understanding of the above description and the examples which follow below certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

EXAMPLE 1

Passive immunization using the FimH variants of the present invention was demonstrated as follows. Anti-serum against FimC and FimCH complexes (using strain J96 (SEQ ID NO: 44) as the source of FimH and strain NU14 as source of FimC) was generated as two different pools and used for these experiments. Mice were passively immunized intraperitoneally with 100 μl each of either anti-C or anti-FimCH rabbit sera 24 hours and 4 hours prior to inoculation. Endpoint titers for the rabbit sera were determined to be at least 1:500,000 by ELISA against the respective antigens.

Bacteria of the respective strains were then collected, washed and re-suspended in phosphate buffered saline (PBS) and cell concentration adjusted to OD=1.8 (at 600 nm). This suspension was then diluted 1:10 in PBS and tested for hemagglutination (HA) with guinea pig erythrocytes. This final suspension was used as inoculum and viability was determined on TSA plates. Mice were anaesthetized and then inoculated intraurethrally with 50 μl of *E. coli* suspension containing about $3\times10^7$ cfu (colony forming units). Two days post-inoculation, the mice were sacrificed and bladders were removed and collected into 500 μl PBS supplemented with 1% mannose. The number of CFU's per bladder was determined by grinding the bladders with a tissue tearer and then diluting and plating the suspension on TSA plates. The mean number of colony forming units per bladder was determined and data transformed to log CFU/bladder (as reported in Table 2).

TABLE 1

SEQ ID NOs. of Nucleotides and Amino acids

| Strain | Nucleotide SEQ ID NO: | Polypeptide SEQ ID NO: |
|---|---|---|
| J96 | 21 | 44 |
| NU14 | 22 | 45 |
| B210 | 1 | 23 |

TABLE 1-continued

SEQ ID NOs. of Nucleotides and Amino acids

| Strain | Nucleotide SEQ ID NO: | Polypeptide SEQ ID NO: |
|---|---|---|
| B212 | 2 | 24 |
| B217 | 3 | 25 |
| B223 | 4 | 26 |
| B228 | 5 | 27 |
| B238 | 6 | 28 |
| B240 | 7 | 29 |
| B242 | 8 | 30 |
| DS17 | 9 | 31 |
| EC42 | 10 | 32 |
| EC45 | 11 | 33 |
| EC56 | 12 | 34 |
| EC58 | 13 | 35 |
| EC60 | 14 | 36 |
| EC61 | 15 | 37 |
| EC62 | 16 | 38 |
| EC80 | 17 | 39 |
| EC89 | 18 | 40 |
| EC95 | 19 | 41 |
| G162 | 54 | 42 |
| G189 | 20 | 43 |
| Consensus | — | 55 |

TABLE 2

Passive Protection by FimH Variants

| Strain | Mean Log CFU per Bladder | | | T-test | |
|---|---|---|---|---|---|
| | FimC | FimCH | Naive | C vs. CH | CH vs. Naive |
| B223 | 7.79 | 5.69 | 7.58 | 0.0034 | 0.0107 |
| EC45 | 6.43 | 4.58 | ND | 0.0087 | ND |
| Nu14 | 4.54 | 2.53 | 5.22 | 0.0014 | 0.0000428 |
| B217 | 4.47 | 3.49 | 5.17 | 0.0142 | 0.0007 |
| DS17 | 4.64 | 3.02 | 4.45 | 0.0163 | 0.0355 |
| B218 | 4.30 | 2.99 | 4.16 | 0.0066 | 0.0331 |
| B220 | 4.18 | 1.93 | 3.55 | 0.0000257 | 0.0016 |
| EC56 | 3.02 | 2.60 | 3.34 | 0.5245 | 0.2222 |
| EC42 | 2.47 | 1.13 | 2.83 | 0.0274 | 0.0013 |
| J96 | 2.09 | 0.96 | 2.29 | 0.1005 | 0.0328 |
| B212 | 3.20 | 2.05 | 3.20 | 0.0167 | 0.443 |

EXAMPLE 2

Construction of Plasmid Vector for FimCH Production

The plasmid vector, pCGA139-1-1, for production of FimCH was constructed in several steps. Although this example is directed to the use of FimH and FimC from J96, the example is also applicable to the FimH variants of the invention.

Construction of pCGA101-8

Genomic DNA was prepared from *Escherichia coli* strain J96. The pellet from 1.0 ml of an overnight culture was washed with PBS, resuspended in 500 μl sterile sucrose Tris EDTA (0.3 molar sucrose: 100 millimolar Tris, pH8.0: 50 millimolar EDTA) and 0.01 μg lysozyme was added thereto. The suspension was incubated at 37° C. for 10 minutes and SDS was added to a final concentration of 0.5%. The mixture was then treated with RNase for 10 minutes at 37° C. after which the DNA was extracted with water saturated phenol followed by a mixture of chloroform: isoamyl alcohol at a 24:1 ratio v/v and ethanol precipitated. The resulting pellet was washed with 70% ethyl alcohol, dried and resuspended in a solution containing 10.0 mM Tris and 0.1 mM EDTA. This DNA was used as template for PCR amplification of the fimC gene.

PCR was performed with primers gal F and ga2R (SEQ ID NO: 56 and 57, respectively) containing NcoI and BglII restriction sites, respectively. Conditions used were: 1 cycle at 95° C. for 1.0 min; 25 cycles of amplification with strand separation at 95° C. for 30 sec, annealing at 50° C. for 30 sec and strand elongation at 72° C. for 2.0 min. This was followed by one 10 min cycle at 72° C. to ensure complete elongation of all ends. PCR products were purified via Qiagen columns and the gene was cloned into the vector pPW19R (construction described below), 3' to the Pel B leader sequence on the plasmid. The result was plasmid pCGA101-8 (shown in FIG. 3).

Construction of pCGA122-30

Figure 4:
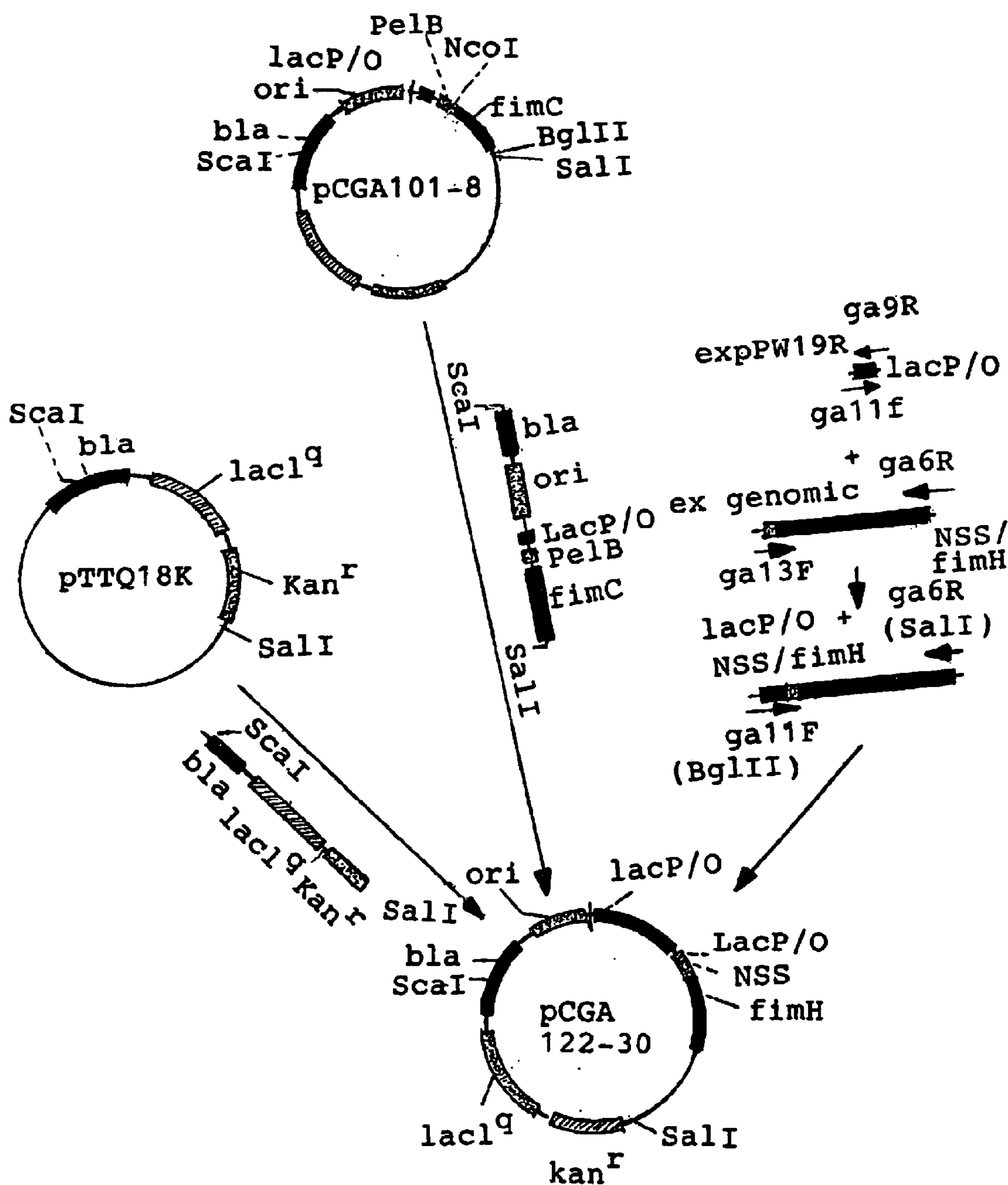
FIG. 4 is a diagram showing the construction of the vector designated as pCGA122-30.

A kanamycin resistance gene was excised as a AlwNI/Styl fragment from pET26b(+) (Novagen) and cloned into the unique Drall site in pTTQ185' of the lacI$^q$ producing pTTQ18K. This plasmid contains the lacI$^q$ and kan$^r$ genes in tandem so they can be cloned as a single cassette (see FIG. 4).

In an effort to obtain optimal yields of FimH, its native signal was used to replace the Pel B leader sequence. A method utilizing overlapping PCR was used. Primary PCR segments were (1) fimH gene and its native signal from genomic J96 DNA with primers ga13F and ga6R (SEQ ID NO: 58 and 59, respectively) and (2) lac promoter/operator (lac p/o) from pPW19R with primers ga11 F and ga9R (SEQ ID NO: 60 and 61, respectively). Overlapping PCR resulted in a single fragment primed with ga11 F and ga6R containing BglII and SalI sites, respectively.

Vector pCGA122-30 was made by ligating (1) the BglII/SalI PCR fragment consisting of lac p/o, fimH native signal sequence+fimH; (2) the BglII/ScaI fragment from pCGA101-8 containing the beta-lactamase gene, pUC ori, lac p/o, pelB leader, and fimC; and (3) the cassette containing lacI$^q$ and kan$^r$ from pTTQ18K as a SalI/ScaI fragment.

Construction of pGA139-1 and Selection of the Final Clone

The PelB signal 5' to fimC was replaced with fimC native signal: primary fragments for fimC native signal replacement were derived from (1) genomic J96 DNA with primers ga24F and ga23R, and (2) lac p/o from pPW19R with primers as mentioned previously. FimC and its native signal were the result of overlapping PCR obtained as one cassette with primers ga24F and ga2R containing AflIII and BglII sites, respectively. The product was cloned as a replacement AflIII/EcoRI to pCGA122-30 producing pCGA126-1 (see FIG. 5 and SEQ ID NO: 46).

Figure 6:
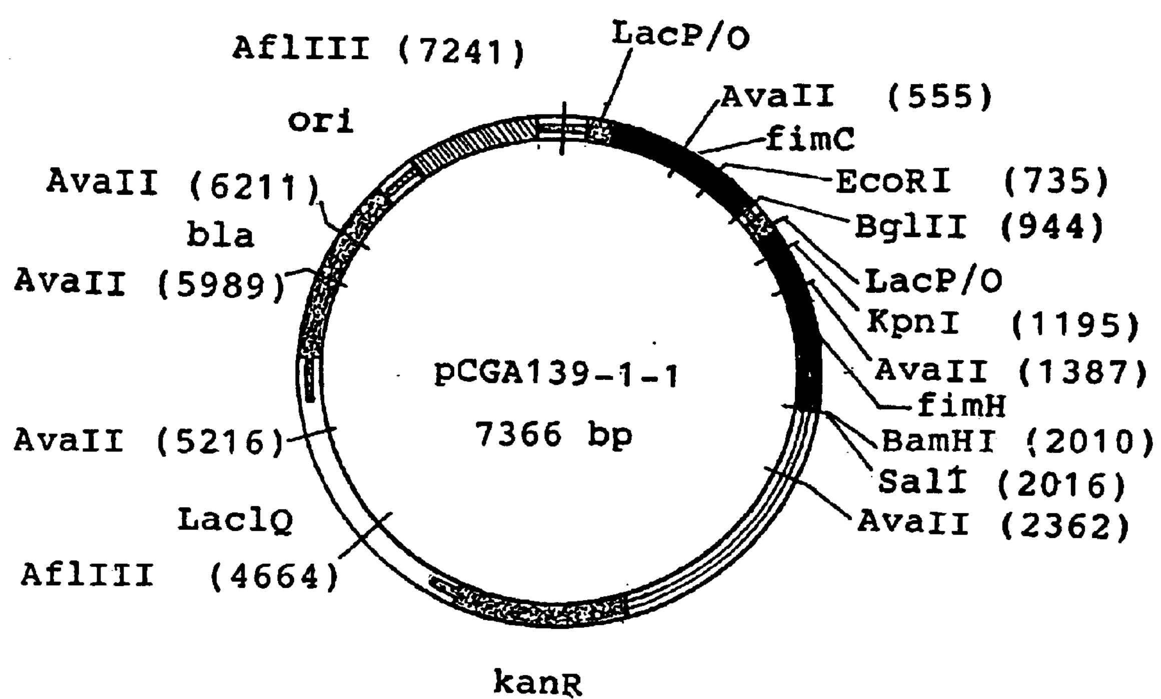
FIG. 6 is a diagram showing the arrangement of genes in the vector designated as pCGA139-1-1.

The beta-lactamase (bla) gene was inactivated by interruption at the ScaI site. This was followed by treatment with an exonuclease (Bal31) and subsequent filling in with deoxynucleotide tri-phosphates (dNTPs). The plasmid was finally re-ligated resulting in a deletion of about 60 bases and thus forming the plasmid pCGA139-1 (see FIGS. 5 and 6).

pCGA126-1 was sequenced in its entirety and the deletion at the ScaI site (thereby giving rise to the pGCA139-1 plasmid) was confirmed by sequencing.

Plasmid pCGA139-1 was transformed into a BL21 *E. coli* host strain to optimize protein expression. Twenty microliters of BL21 competent cells were pipetted into a pre-chilled 1.5 ml polypropylene tube. One microliter of vector was added and the mixture was incubated on ice for 5 min. The cells were heat shocked in a 42° C. water bath for exactly 30 sec followed by incubation on ice for 2 min. SOC medium (80 μl) was added followed by incubation at 37° C. with shaking at 250 rpm for 1 hr. The culture was plated on 2XYT agar containing 50 μg/ml kanamycin and plates were incubated overnight at 37° C. The recipes for terrific medium and SOC broth can be found in standard books on cell culture (for example, see Sambrook et al (1989), supra, at book 3, appendix page A.2.).

Plasmid preparations and frozen 15–20% glycerol stocks were made from individual colonies grown overnight in terrific broth. Candidates were chosen by both the absence of the ScaI site and by sensitivity to 50 μg/ml ampicilin. Plasmids were further analyzed for production of target protein. pCGA139-1 was cloned by plating on 2XYT agar containing 50 μg/ml kanamycin. Six clones were analyzed according to their restriction patterns, Western blot analysis, and production of FimCH protein. A single colony was grown overnight in broth and stored in 15%–20% sterile glycerol in Nunc vials at a temperature of −70° C.

Overnight cultures were diluted 1:30 in terrific broth containing 50 μg/ml kanamycin and grown at 37° C. to mid-log phase (about 0.3 at $OD_{600}$). Fifteen ml of each culture was induced with 2.0 mM IPTG and harvested after 3 hr. Several 1 ml aliquots from each sample were sedimented in an eppendorf centrifuge at 14,000 rpm for 2 min. Total protein was estimated by BCA assay and 1.0 μg total protein of uninduced and induced culture was loaded to two polyacrylamide gels for electrophoresis against FimCH standards of known concentration. FimC and FimH were assayed on separate gels/membranes. Samples were also assayed via ion exchange chromatography for levels of FimCH protein.

Proteins were transferred to nitrocellulose membranes via Western blot, blocked with 2% dried milk and treated with primary polyclonal antibodies to FimC or FimH-T3. Membranes were washed 3×(15 min each wash) with PBS plus 0.01% Tween 20 after which a donkey anti-rabbit secondary antibody conjugated to horseradish peroxidase (HRP) was applied for 1 hr. Membranes were washed as described before followed by treatment with an anti-HRP detection reagent, ECL, or ECL-plus. Nitrocellulose was finally exposed to x-ray films and developed in a M35-A x-omatic processor.

For ion exchange chromatography of the FimCH product, all samples were resuspended in 200 μl of PBS, sonicated for 12 min, and diluted 4 fold with PBS. Each sample was centrifuged at 10,000 rpm for 3 min into a 0.45 micron spin filter unit and transferred into HPLC microvials for analysis. A Pharmacia Mono-S HR 5/5 column (5 mm×50 mm) was used for the quantification of pilus proteins in analyzed samples. Mobile phase A was 20 mM potassium phosphate (pH 7.0); mobile phase B was mobile phase A but containing 0.5 M potassium chloride. A gradient of 0%–30% B over 20 minutes was run at a flow rate of 1.25 ml/min. Eluted protein was detected using intrinsic tryptophan fluorescence detection (excitation 280 nm, emission 335 nm). A standard curve was generated using reference standard material diluted to concentrations from 5.2 μg/ml to 15.6 μg/ml. The correlation coefficient of the calibration curve was >0.995. The concentration of FimCH was determined using regression analysis from a standard curve of the area under the product peak.

Construction of Vector pPW19R

This vector was constructed by inserting an intergenic region derived from pPW14R as a Not1-Nco1 fragment into pPW19 creating an additional lacP/O, RBS, and PelB leader. pPW19 represents a modification of the vector pPW16, which was made by cloning the coding sequence for the c-myc epitope into pPW8 as a Not1-Sal1 linker.

pPW8 is a modification of pPW6, which is a derivative of pPW4, the latter being engineered by insertion of a 60 bp synthetic linker containing a Not1 site, a 4D4 epitope sequence, and a termination codon into pPW2 as a BamHI-SalI fragment.

pPW2 was made by cloning the full length gene3 (from pSPLIII (JAS)) into pPW1, the latter prepared by cloning the PelB leader sequence (an amino terminal sequence directing periplasmic insertion of pectin lysate in *E. coli*) into the vector pUC118.

TABLE 3

Primer Sequences used for Vector Construction.

| Primer* | Sequence | SEQ ID NO: |
|---|---|---|
| GA1F | 5'-CCTGCCATGGCGGGTGTGGCGCTGGGTGCGA CCCGCGTGATTTATCCGGCAGGGC-3' | 56 |
| GA2R | 5'-GGCGTCGACAGATTCTATTATTCCATTACGC CCGTC-3' | 57 |
| GA13F | 5'-CACACAGGAAACAGCTATGATTGTAATGAAA ACGAG-3' | 58 |
| GA6R | 5'-GGCGTCGACGGATCCTTATTGATAAACAAAA GTCACGCC-3' | 59 |
| GA11F | 5'-CCGAATAAAGATATCACGACAGGTTTCCCG-3' | 60 |
| GA9R | 5'-CATAGCTGTTTCCTGTGTG-3' | 61 |
| GA24F | 5'-TGCTCACATGTTCTTTCCTGCGT-3' | 62 |
| GA23R | 5'-GACGTTTTTATTACTCATAGCTGTTTCCTGTGTG-3' | 63 |
| GA21F | 5'-ATGAGTAATAAAAACGTCAATGTAAGGAAA TCGCAGG-3' | 64 |

*"F" refers to forward primers and "R" refers to reverse primers.

The nucleotide sequences corresponding to the structures used in cloning FimCH were as follows: SEQ ID NO: 47 shows J96 FimC plus a signal sequence and SEQ ID NO: 48 shows J96 FimH; SEQ ID NO: 49 shows the sequence for the kanamycin resistance gene; SEQ ID NO: 50 shows the sequence for lac IQ; SEQ ID NO: 51 shows the sequence of Beta-lactamase (with the deletions described in Example 2 covering residues 285–335), SEQ ID NO: 52 shows the sequence of the origin of replication, and SEQ ID NO: 53 shows the sequence of Lac p/o (where the two promoter sequences are found at (1) residues 100 to 215, and (2) residues 990 to 1105 of the plasmid (SEQ ID NO: 46)).

Thus, the present invention also relates to a new method of preparing polypeptides from recombinant cells using a vector comprising the plasmid of FIGS. 3 through 6. In specific embodiments, the polypeptides comprise the amino acid sequences of FIG. 2. In one embodiment, this process and plasmid can be used to prepare polypeptides that comprise a bacterial chaperone, such as FimC, fused to a bacterial adhesin, such as FimH or any of the polypeptides presented in FIG. 2, including any consensus sequence derived therefrom. The plasmid based procedure of the invention can be used to prepare any polypeptides but especially finds use in preparing the chaperone complexes of the adhesin proteins presented herein. Thus, for example, large amounts of FimCH, the complex of the periplasmic bacterial chaperone, FimC, and the bacterial adhesin, FimH, are readily prepared using the processes disclosed herein.

Numerous modifications and variants of the invention are possible in light of the above teachings; therefore, within the scope of the appended claims, the invention may be practiced otherwise than as specifically described.

What is claimed is:

1. An isolated polypeptide comprising residues 26 to 186 of SEQ ID NO: 29, wherein said polypeptide induces an antibody response that recognizes the polypeptide SEQ ID NO: 29.

2. An isolated polypeptide comprising amino acids 1 to 186 of SEQ ID NO: 29, wherein said polypeptide induces an antibody response that recognizes the polypeptide SEQ ID NO: 29.

3. An isolated immunogenic polypeptide comprising the amino acid sequence of SEQ ID NO: 29.

4. A vaccine composition comprising an effective amount of the polypeptide of claims 1, 2, or 3, wherein said polypeptide is in a pharmaceutically acceptable carrier.

* * * * *